(12) United States Patent
Layman

(10) Patent No.: US 8,956,574 B2
(45) Date of Patent: Feb. 17, 2015

(54) GAS DELIVERY SYSTEM WITH CONSTANT OVERPRESSURE RELATIVE TO AMBIENT TO SYSTEM WITH VARYING VACUUM SUCTION

(75) Inventor: Fredrick P. Layman, Carefree, AZ (US)

(73) Assignee: SDCmaterials, Inc., Tempe, AZ (US)

( * ) Notice: Subject to any disclaimer, the term of this patent is extended or adjusted under 35 U.S.C. 154(b) by 154 days.

(21) Appl. No.: 12/879,853

(22) Filed: Sep. 10, 2010

(65) Prior Publication Data

US 2011/0006463 A1 Jan. 13, 2011

Related U.S. Application Data

(62) Division of application No. 12/152,097, filed on May 9, 2008.

(60) Provisional application No. 60/928,946, filed on May 11, 2007.

(51) Int. Cl.
| | |
|---|---|
| *B01J 19/08* | (2006.01) |
| *B01J 19/00* | (2006.01) |
| *B22F 9/12* | (2006.01) |
| *F28D 15/00* | (2006.01) |
| *F28F 27/00* | (2006.01) |
| *B01J 25/00* | (2006.01) |
| *B01J 25/02* | (2006.01) |
| *F28D 7/02* | (2006.01) |
| *F28D 7/08* | (2006.01) |

(52) U.S. Cl.
CPC ............... *B01J 19/0013* (2013.01); *B22F 9/12* (2013.01); *F28D 15/00* (2013.01); *F28F 27/00* (2013.01); *B01J 25/00* (2013.01); *B01J 25/02* (2013.01); *B22F 2999/00* (2013.01); *F28D 7/024* (2013.01); *F28D 7/08* (2013.01); *Y10S 623/92* (2013.01); *Y10S 623/923* (2013.01)
USPC ....... 422/186.03; 422/186; 623/920; 623/923

(58) Field of Classification Search
USPC .............. 422/186, 186.03; 977/844; 429/443, 429/444; 427/446
See application file for complete search history.

(56) References Cited

U.S. PATENT DOCUMENTS

| | | | |
|---|---|---|---|
| 2,284,554 A | 5/1942 | Beyerstedt | |
| 2,419,042 A | 4/1947 | Todd | 202/205 |
| 2,519,531 A | 8/1950 | Worn | 230/95 |
| 2,562,753 A | 7/1951 | Trost | 241/39 |
| 2,689,780 A | 9/1954 | Rice | 23/106 |
| 3,001,402 A | 9/1961 | Koblin | 73/421.5 |
| 3,067,025 A | 12/1962 | Chisholm | 75/84.5 |
| 3,145,287 A | 8/1964 | Siebein et al. | |
| 3,178,121 A | 4/1965 | Wallace, Jr. | 241/5 |
| 3,179,782 A | 4/1965 | Matvay | |
| 3,313,908 A | 4/1967 | Unger et al. | |
| 3,401,465 A | 9/1968 | Larwill | 34/57 |
| 3,450,926 A | 6/1969 | Kiernan | |
| 3,457,788 A | 7/1969 | Miyajima | 73/422 |
| 3,537,513 A | 11/1970 | Austin | 165/70 |
| 3,741,001 A | 6/1973 | Fletcher et al. | 73/28 |
| 3,752,172 A | 8/1973 | Cohen et al. | |
| 3,774,442 A | 11/1973 | Gustavsson | 73/28 |
| 3,830,756 A | 8/1974 | Sanchez et al. | |
| 3,871,448 A | 3/1975 | Vann et al. | |
| 3,892,882 A | 7/1975 | Guest et al. | |
| 3,914,573 A | 10/1975 | Muehlberger | |
| 3,959,420 A | 5/1976 | Geddes et al. | 261/112 |
| 3,969,482 A | 7/1976 | Teller | |
| 4,008,620 A | 2/1977 | Narato et al. | 73/421.5 A |
| 4,018,388 A | 4/1977 | Andrews | 241/39 |
| 4,139,497 A | 2/1979 | Castor et al. | 252/470 |
| 4,157,316 A | 6/1979 | Thompson et al. | |
| 4,171,288 A | 10/1979 | Keith et al. | 252/462 |
| 4,174,298 A | 11/1979 | Antos | |
| 4,227,928 A | 10/1980 | Wang | |
| 4,248,387 A | 2/1981 | Andrews | 241/5 |
| 4,253,917 A | 3/1981 | Wang | |
| 4,284,609 A | 8/1981 | deVries | 423/242 |
| 4,369,167 A | 1/1983 | Weir, Jr. | |

(Continued)

FOREIGN PATENT DOCUMENTS

| | | | |
|---|---|---|---|
| JP | 56-146804 A | 11/1981 | |
| JP | 61-086815 A | 5/1986 | |

(Continued)

OTHER PUBLICATIONS

A. Gutsch et al., "Gas-Phase Production of Nanoparticles", Kona No. 20, 2002, pp. 24-37.

(Continued)

*Primary Examiner* — Natalia Levkovich
(74) *Attorney, Agent, or Firm* — Morrison & Foerster LLP

(57) ABSTRACT

A system operating in an environment having an ambient pressure, the system comprising: a reactor configured to combine a plasma stream, powder particles and conditioning fluid to alter the powder particles and form a mixture stream; a supply chamber coupled to the reactor; a suction generator configured to generate a suction force at the outlet of the reactor; a fluid supply module configured to supply the conditioning fluid at an original pressure; and a pressure regulation module configured to: receive the conditioning fluid from the fluid supply module, reduce the pressure of the conditioning fluid from the original pressure to a selected pressure relative to the ambient pressure regardless of any changes in the suction force at the outlet of the reactor, and supply the conditioning fluid at the selected pressure to the supply chamber.

22 Claims, 5 Drawing Sheets

(56) References Cited

U.S. PATENT DOCUMENTS

| | | | |
|---|---|---|---|
| 4,388,274 A | 6/1983 | Rourke et al. | 422/177 |
| 4,431,750 A | 2/1984 | McGinnis et al. | |
| 4,436,075 A | 3/1984 | Campbell et al. | 123/557 |
| 4,458,138 A | 7/1984 | Adrian et al. | |
| 4,459,327 A | 7/1984 | Wang | |
| 4,505,945 A | 3/1985 | Dubust et al. | |
| 4,513,149 A | 4/1985 | Gray et al. | 564/449 |
| 4,731,517 A | 3/1988 | Cheney | |
| 4,764,283 A | 8/1988 | Ashbrook et al. | 210/695 |
| 4,765,805 A | 8/1988 | Wahl et al. | |
| 4,824,624 A | 4/1989 | Palicka et al. | 264/67 |
| 4,855,505 A | 8/1989 | Koll | 564/398 |
| 4,866,240 A | 9/1989 | Webber | |
| 4,885,038 A | 12/1989 | Anderson et al. | |
| 4,983,555 A | 1/1991 | Roy et al. | 501/120 |
| 4,987,033 A | 1/1991 | Abkowitz et al. | 428/469 |
| 5,015,863 A | 5/1991 | Takeshima et al. | |
| 5,041,713 A | 8/1991 | Weidman | |
| 5,043,548 A | 8/1991 | Whitney et al. | 219/121.84 |
| 5,070,064 A | 12/1991 | Hsu et al. | |
| 5,073,193 A | 12/1991 | Chaklader et al. | 75/346 |
| 5,157,007 A | 10/1992 | Domesle et al. | |
| 5,230,844 A | 7/1993 | Macaire et al. | |
| 5,338,716 A | 8/1994 | Triplett et al. | |
| 5,369,241 A | 11/1994 | Taylor et al. | 219/121.47 |
| 5,371,049 A | 12/1994 | Moffett et al. | 501/89 |
| 5,372,629 A | 12/1994 | Anderson et al. | 75/332 |
| 5,392,797 A | 2/1995 | Welch | 134/108 |
| 5,439,865 A | 8/1995 | Abe et al. | 502/333 |
| 5,442,153 A | 8/1995 | Marantz et al. | |
| 5,460,701 A | 10/1995 | Parker et al. | |
| 5,464,458 A | 11/1995 | Yamamoto | |
| 5,485,941 A | 1/1996 | Guyomard et al. | 222/1 |
| 5,534,149 A | 7/1996 | Birkenbeil et al. | 210/636 |
| 5,553,507 A | 9/1996 | Basch et al. | 73/863.01 |
| 5,562,966 A | 10/1996 | Clarke et al. | |
| 5,582,807 A | 12/1996 | Liao et al. | |
| 5,611,896 A | 3/1997 | Swanepoel et al. | 204/169 |
| 5,630,322 A | 5/1997 | Heilmann et al. | 62/95 |
| 5,652,304 A | 7/1997 | Mizrahi | |
| 5,726,414 A | 3/1998 | Kitahashi et al. | |
| 5,749,938 A | 5/1998 | Coombs | 75/332 |
| 5,776,359 A | 7/1998 | Schultz et al. | 252/62.51 |
| 5,788,738 A | 8/1998 | Pirzada et al. | 75/331 |
| 5,811,187 A | 9/1998 | Anderson et al. | 428/403 |
| 5,837,959 A | 11/1998 | Muehlberger et al. | |
| 5,851,507 A * | 12/1998 | Pirzada et al. | 423/659 |
| 5,853,815 A | 12/1998 | Muehlberger | 427/446 |
| 5,905,000 A | 5/1999 | Yadav et al. | 429/33 |
| 5,935,293 A | 8/1999 | Detering et al. | 75/10.29 |
| 5,989,648 A | 11/1999 | Phillips | 427/456 |
| 5,993,967 A | 11/1999 | Brotzman, Jr. et al. | 428/407 |
| 5,993,988 A | 11/1999 | Ohara et al. | 429/40 |
| 6,012,647 A | 1/2000 | Ruta et al. | 239/132.1 |
| 6,033,781 A | 3/2000 | Brotzman, Jr. et al. | 428/405 |
| 6,045,765 A | 4/2000 | Nakatsuji et al. | |
| 6,059,853 A | 5/2000 | Coombs | 75/332 |
| 6,102,106 A | 8/2000 | Manning et al. | 165/76 |
| 6,117,376 A | 9/2000 | Merkel | |
| 6,213,049 B1 | 4/2001 | Yang | |
| 6,214,195 B1 | 4/2001 | Yadav et al. | 205/334 |
| 6,228,904 B1 | 5/2001 | Yadav et al. | 523/210 |
| 6,254,940 B1 | 7/2001 | Pratsinis et al. | 427/562 |
| 6,261,484 B1 | 7/2001 | Phillips et al. | 264/5 |
| 6,267,864 B1 | 7/2001 | Yadav et al. | 205/341 |
| 6,322,756 B1 | 11/2001 | Arno et al. | |
| 6,342,465 B1 | 1/2002 | Klein et al. | |
| 6,344,271 B1 | 2/2002 | Yadav et al. | 428/402 |
| 6,379,419 B1 | 4/2002 | Celik et al. | 75/346 |
| 6,387,560 B1 | 5/2002 | Yadav et al. | 429/45 |
| 6,395,214 B1 | 5/2002 | Kear et al. | 264/434 |
| 6,398,843 B1 | 6/2002 | Tarrant | 75/249 |
| 6,409,851 B1 | 6/2002 | Sethuram et al. | 148/565 |
| 6,413,781 B1 | 7/2002 | Geis et al. | 436/178 |
| 6,416,818 B1 | 7/2002 | Aikens et al. | 427/383.1 |
| RE37,853 E | 9/2002 | Detering et al. | 75/10.19 |
| 6,444,009 B1 | 9/2002 | Liu et al. | 75/332 |
| 6,475,951 B1 | 11/2002 | Domesle et al. | |
| 6,517,800 B1 | 2/2003 | Cheng et al. | 423/447.1 |
| 6,524,662 B2 | 2/2003 | Jang et al. | 427/535 |
| 6,531,704 B2 | 3/2003 | Yadav et al. | 250/493.1 |
| 6,548,445 B1 | 4/2003 | Buysch et al. | |
| 6,554,609 B2 | 4/2003 | Yadav et al. | 432/9 |
| 6,562,304 B1 | 5/2003 | Mizrahi | |
| 6,562,495 B2 | 5/2003 | Yadav et al. | 429/12 |
| 6,569,397 B1 | 5/2003 | Yadav et al. | 423/345 |
| 6,569,518 B2 | 5/2003 | Yadav et al. | 428/323 |
| 6,572,672 B2 | 6/2003 | Yadav et al. | 75/343 |
| 6,579,446 B1 * | 6/2003 | Teran et al. | 210/85 |
| 6,596,187 B2 | 7/2003 | Coll et al. | |
| 6,603,038 B1 | 8/2003 | Hagemeyer et al. | 560/241.1 |
| 6,607,821 B2 | 8/2003 | Yadav et al. | 428/323 |
| 6,610,355 B2 | 8/2003 | Yadav et al. | 427/115 |
| 6,623,559 B2 | 9/2003 | Huang | |
| 6,635,357 B2 | 10/2003 | Moxson et al. | 428/548 |
| 6,641,775 B2 | 11/2003 | Vigliotti et al. | 264/618 |
| 6,652,822 B2 | 11/2003 | Phillips et al. | 423/290 |
| 6,652,967 B2 | 11/2003 | Yadav et al. | 428/403 |
| 6,669,823 B1 | 12/2003 | Sarkas et al. | 204/164 |
| 6,682,002 B2 | 1/2004 | Kyotani | 239/318 |
| 6,689,192 B1 | 2/2004 | Phillips et al. | 75/342 |
| 6,699,398 B1 | 3/2004 | Kim | 216/55 |
| 6,706,097 B2 | 3/2004 | Zornes | 96/153 |
| 6,706,660 B2 | 3/2004 | Park | |
| 6,710,207 B2 | 3/2004 | Bogan, Jr. et al. | |
| 6,713,176 B2 | 3/2004 | Yadav et al. | 428/402 |
| 6,716,525 B1 | 4/2004 | Yadav et al. | 428/402 |
| 6,746,791 B2 | 6/2004 | Yadav et al. | 429/30 |
| 6,772,584 B2 | 8/2004 | Chun et al. | 60/275 |
| 6,786,950 B2 | 9/2004 | Yadav et al. | 75/346 |
| 6,813,931 B2 | 11/2004 | Yadav et al. | 73/31.05 |
| 6,817,388 B2 | 11/2004 | Tsangaris et al. | 141/82 |
| 6,832,735 B2 | 12/2004 | Yadav et al. | 241/16 |
| 6,838,072 B1 | 1/2005 | Kong et al. | 423/594.2 |
| 6,855,410 B2 | 2/2005 | Buckley | |
| 6,855,426 B2 | 2/2005 | Yadav | 428/403 |
| 6,855,749 B1 | 2/2005 | Yadav et al. | 523/105 |
| 6,886,545 B1 | 5/2005 | Holm | 123/568.21 |
| 6,896,958 B1 | 5/2005 | Cayton et al. | 428/323 |
| 6,902,699 B2 | 6/2005 | Fritzemeier et al. | 419/38 |
| 6,916,872 B2 | 7/2005 | Yadav et al. | 524/430 |
| 6,919,527 B2 | 7/2005 | Boulos et al. | 219/121.52 |
| 6,933,331 B2 | 8/2005 | Yadav et al. | 523/210 |
| 6,972,115 B1 | 12/2005 | Ballard | |
| 6,986,877 B2 | 1/2006 | Takikawa et al. | 423/447.3 |
| 6,994,837 B2 | 2/2006 | Boulos et al. | 423/613 |
| 7,007,872 B2 | 3/2006 | Yadav et al. | 241/1 |
| 7,022,305 B2 | 4/2006 | Drumm et al. | |
| 7,052,777 B2 | 5/2006 | Brotzman, Jr. et al. | 428/570 |
| 7,073,559 B2 | 7/2006 | O'Larey et al. | 164/76.1 |
| 7,081,267 B2 | 7/2006 | Yadav | 427/115 |
| 7,101,819 B2 | 9/2006 | Rosenflanz et al. | 501/10 |
| 7,147,544 B2 | 12/2006 | Rosenflanz | 451/28 |
| 7,147,894 B2 | 12/2006 | Zhou et al. | 427/256 |
| 7,166,198 B2 | 1/2007 | Van Der Walt et al. | 204/165 |
| 7,166,663 B2 | 1/2007 | Cayton et al. | 524/430 |
| 7,172,649 B2 | 2/2007 | Conrad et al. | 106/35 |
| 7,172,790 B2 | 2/2007 | Koulik et al. | |
| 7,178,747 B2 | 2/2007 | Yadav et al. | 241/23 |
| 7,208,126 B2 | 4/2007 | Musick et al. | 423/69 |
| 7,211,236 B2 | 5/2007 | Stark et al. | 423/592.1 |
| 7,217,407 B2 | 5/2007 | Zhang | 423/610 |
| 7,220,398 B2 | 5/2007 | Sutorik et al. | 423/593.1 |
| 7,307,195 B2 | 12/2007 | Polverejan et al. | 585/443 |
| 7,323,655 B2 | 1/2008 | Kim | 219/121.43 |
| 7,384,447 B2 | 6/2008 | Kodas et al. | 75/332 |
| 7,417,008 B2 | 8/2008 | Richards et al. | |
| 7,494,527 B2 | 2/2009 | Jurewicz et al. | 75/346 |
| 7,541,012 B2 | 6/2009 | Yeung et al. | |
| 7,541,310 B2 | 6/2009 | Espinoza et al. | |
| 7,572,315 B2 | 8/2009 | Boulos et al. | 75/336 |
| 7,611,686 B2 | 11/2009 | Alekseeva et al. | |
| 7,615,097 B2 | 11/2009 | McKechnie et al. | 75/346 |
| 7,618,919 B2 | 11/2009 | Shimazu et al. | |

(56) References Cited

U.S. PATENT DOCUMENTS

| | | | |
|---|---|---|---|
| 7,622,693 B2 | 11/2009 | Foret | 219/121.43 |
| 7,678,419 B2 | 3/2010 | Kevwitch et al. | |
| 7,803,210 B2 | 9/2010 | Sekine et al. | |
| 7,874,239 B2 | 1/2011 | Howland | |
| 7,897,127 B2 | 3/2011 | Layman et al. | |
| 7,905,942 B1 | 3/2011 | Layman | |
| 8,051,724 B1 | 11/2011 | Layman et al. | |
| 8,076,258 B1 | 12/2011 | Biberger | |
| 8,142,619 B2 | 3/2012 | Layman et al. | |
| 2001/0042802 A1 | 11/2001 | Youds | 241/5 |
| 2002/0018815 A1 | 2/2002 | Sievers et al. | 424/489 |
| 2002/0068026 A1 | 6/2002 | Murrell et al. | 422/211 |
| 2002/0079620 A1 | 6/2002 | DuBuis et al. | 264/328.14 |
| 2002/0100751 A1* | 8/2002 | Carr | 219/209 |
| 2002/0102674 A1 | 8/2002 | Anderson | 435/174 |
| 2002/0131914 A1 | 9/2002 | Sung | |
| 2002/0143417 A1 | 10/2002 | Ito et al. | |
| 2002/0182735 A1 | 12/2002 | Kibby et al. | |
| 2002/0183191 A1 | 12/2002 | Faber et al. | |
| 2002/0192129 A1 | 12/2002 | Shamouilian et al. | |
| 2003/0036786 A1 | 2/2003 | Duren et al. | 607/96 |
| 2003/0042232 A1 | 3/2003 | Shimazu | |
| 2003/0066800 A1 | 4/2003 | Saim et al. | 264/5 |
| 2003/0108459 A1 | 6/2003 | Wu et al. | 422/186.04 |
| 2003/0110931 A1 | 6/2003 | Aghajanian et al. | |
| 2003/0139288 A1 | 7/2003 | Cai et al. | |
| 2003/0143153 A1 | 7/2003 | Boulos et al. | |
| 2003/0172772 A1 | 9/2003 | Sethuram et al. | |
| 2003/0223546 A1 | 12/2003 | McGregor et al. | 378/143 |
| 2004/0009118 A1 | 1/2004 | Phillips et al. | 423/592.1 |
| 2004/0023302 A1 | 2/2004 | Archibald et al. | |
| 2004/0023453 A1 | 2/2004 | Xu et al. | 257/369 |
| 2004/0077494 A1 | 4/2004 | LaBarge et al. | 502/303 |
| 2004/0103751 A1 | 6/2004 | Joseph et al. | 75/10.19 |
| 2004/0119064 A1 | 6/2004 | Narayan et al. | |
| 2004/0127586 A1 | 7/2004 | Jin et al. | |
| 2004/0167009 A1 | 8/2004 | Kuntz et al. | 501/95.2 |
| 2004/0176246 A1 | 9/2004 | Shirk et al. | |
| 2004/0208805 A1 | 10/2004 | Fincke et al. | |
| 2004/0213998 A1 | 10/2004 | Hearley et al. | |
| 2004/0238345 A1 | 12/2004 | Koulik et al. | |
| 2004/0251017 A1 | 12/2004 | Pillion et al. | 165/289 |
| 2004/0251241 A1 | 12/2004 | Blutke et al. | |
| 2005/0000321 A1 | 1/2005 | O'Larey et al. | 75/952 |
| 2005/0000950 A1 | 1/2005 | Schroder et al. | 219/121.59 |
| 2005/0066805 A1 | 3/2005 | Park et al. | |
| 2005/0077034 A1 | 4/2005 | King | 165/163 |
| 2005/0097988 A1 | 5/2005 | Kodas et al. | 75/332 |
| 2005/0106865 A1* | 5/2005 | Chung et al. | 438/685 |
| 2005/0163673 A1 | 7/2005 | Johnson et al. | |
| 2005/0199739 A1 | 9/2005 | Kuroda et al. | |
| 2005/0220695 A1 | 10/2005 | Abatzoglou et al. | 423/445 |
| 2005/0227864 A1 | 10/2005 | Sutorik et al. | |
| 2005/0240069 A1 | 10/2005 | Polverejan et al. | 585/444 |
| 2005/0258766 A1 | 11/2005 | Kim | 315/111.21 |
| 2005/0275143 A1 | 12/2005 | Toth | |
| 2006/0051505 A1 | 3/2006 | Kortshagen et al. | 427/212 |
| 2006/0068989 A1 | 3/2006 | Ninomiya et al. | 502/339 |
| 2006/0094595 A1 | 5/2006 | Labarge | |
| 2006/0096393 A1 | 5/2006 | Pesiri | |
| 2006/0105910 A1 | 5/2006 | Zhou et al. | 502/338 |
| 2006/0108332 A1 | 5/2006 | Belashchenko | 219/121.47 |
| 2006/0153728 A1 | 7/2006 | Schoenung et al. | 419/32 |
| 2006/0153765 A1 | 7/2006 | Pham-Huu et al. | 423/345 |
| 2006/0159596 A1 | 7/2006 | De La Veaux et al. | 422/151 |
| 2006/0166809 A1 | 7/2006 | Malek et al. | |
| 2006/0222780 A1 | 10/2006 | Gurevich et al. | |
| 2006/0231525 A1 | 10/2006 | Asakawa et al. | 216/56 |
| 2007/0048206 A1 | 3/2007 | Hung et al. | |
| 2007/0049484 A1 | 3/2007 | Kear et al. | |
| 2007/0063364 A1 | 3/2007 | Hsiao et al. | 264/5 |
| 2007/0084308 A1 | 4/2007 | Nakamura et al. | 75/346 |
| 2007/0084834 A1 | 4/2007 | Hanus et al. | 219/121.5 |
| 2007/0087934 A1 | 4/2007 | Martens et al. | 502/214 |
| 2007/0163385 A1 | 7/2007 | Takahashi et al. | |
| 2007/0173403 A1 | 7/2007 | Koike et al. | 502/300 |
| 2007/0178673 A1 | 8/2007 | Gole et al. | |
| 2007/0253874 A1 | 11/2007 | Foret | 422/186.07 |
| 2007/0292321 A1 | 12/2007 | Plischke et al. | |
| 2008/0006954 A1 | 1/2008 | Yubuta et al. | |
| 2008/0031806 A1 | 2/2008 | Gavenonis et al. | |
| 2008/0038578 A1 | 2/2008 | Li | |
| 2008/0064769 A1 | 3/2008 | Sato et al. | |
| 2008/0105083 A1 | 5/2008 | Nakamura et al. | 75/255 |
| 2008/0116178 A1 | 5/2008 | Weidman | |
| 2008/0125308 A1 | 5/2008 | Fujdala et al. | |
| 2008/0138651 A1 | 6/2008 | Doi et al. | |
| 2008/0175936 A1 | 7/2008 | Tokita et al. | |
| 2008/0206562 A1 | 8/2008 | Stucky et al. | |
| 2008/0207858 A1 | 8/2008 | Kowaleski et al. | |
| 2008/0274344 A1 | 11/2008 | Vieth et al. | |
| 2008/0277092 A1 | 11/2008 | Layman et al. | |
| 2008/0277266 A1 | 11/2008 | Layman | |
| 2008/0277267 A1 | 11/2008 | Biberger et al. | |
| 2008/0277268 A1 | 11/2008 | Layman | |
| 2008/0277269 A1 | 11/2008 | Layman et al. | |
| 2008/0277270 A1 | 11/2008 | Biberger et al. | |
| 2008/0277271 A1 | 11/2008 | Layman et al. | 422/130 |
| 2008/0280049 A1 | 11/2008 | Kevwitch et al. | |
| 2008/0280751 A1 | 11/2008 | Harutyunyan et al. | |
| 2008/0280756 A1 | 11/2008 | Biberger | |
| 2009/0010801 A1 | 1/2009 | Murphy et al. | |
| 2009/0054230 A1 | 2/2009 | Veeraraghavan et al. | |
| 2009/0088585 A1 | 4/2009 | Schammel et al. | |
| 2009/0114568 A1 | 5/2009 | Trevino et al. | |
| 2009/0162991 A1 | 6/2009 | Beneyton et al. | |
| 2009/0168506 A1 | 7/2009 | Han et al. | |
| 2009/0170242 A1 | 7/2009 | Lin et al. | |
| 2009/0181474 A1 | 7/2009 | Nagai | |
| 2009/0200180 A1 | 8/2009 | Capote et al. | |
| 2009/0253037 A1 | 10/2009 | Park et al. | |
| 2009/0274903 A1 | 11/2009 | Addiego | |
| 2009/0286899 A1 | 11/2009 | Hofmann et al. | |
| 2010/0089002 A1 | 4/2010 | Merkel | |
| 2010/0275781 A1 | 11/2010 | Tsangaris | |
| 2011/0006463 A1 | 1/2011 | Layman | |
| 2011/0143041 A1 | 6/2011 | Layman et al. | |
| 2011/0143915 A1 | 6/2011 | Yin et al. | |
| 2011/0143916 A1 | 6/2011 | Leamon | |
| 2011/0143926 A1 | 6/2011 | Yin et al. | |
| 2011/0143930 A1 | 6/2011 | Yin et al. | |
| 2011/0143933 A1 | 6/2011 | Yin et al. | |
| 2011/0144382 A1 | 6/2011 | Yin et al. | |
| 2011/0152550 A1 | 6/2011 | Grey et al. | |
| 2011/0158871 A1 | 6/2011 | Arnold et al. | |
| 2011/0174604 A1 | 7/2011 | Duesel et al. | |
| 2011/0247336 A9 | 10/2011 | Farsad et al. | |
| 2012/0045373 A1 | 2/2012 | Biberger | |
| 2012/0171098 A1 | 7/2012 | Hung et al. | |

FOREIGN PATENT DOCUMENTS

| | | |
|---|---|---|
| JP | 63-214342 A | 9/1988 |
| JP | 05-228361 A | 9/1993 |
| JP | 05-324094 A | 12/1993 |
| JP | H6-065772 | 9/1994 |
| JP | 7031873 A | 2/1995 |
| JP | 07-256116 | 10/1995 |
| JP | 11-502760 A | 3/1999 |
| JP | 2000-220978 A | 8/2000 |
| JP | 2004-233007 A | 8/2004 |
| JP | 2004-249206 A | 9/2004 |
| JP | 2004-290730 A | 10/2004 |
| JP | 2005-503250 A | 2/2005 |
| JP | 2005-122621 A | 5/2005 |
| JP | 2005-218937 A | 8/2005 |
| JP | 2005-342615 A | 12/2005 |
| JP | 2006-001779 A | 1/2006 |
| JP | 2006-508885 A | 3/2006 |
| JP | 2006-247446 A | 9/2006 |
| JP | 2006-260385 A | 9/2006 |
| SU | 493241 | 3/1976 |
| TW | 201023207 | 6/2010 |
| WO | WO-96/28577 A1 | 9/1996 |

(56) References Cited

FOREIGN PATENT DOCUMENTS

| WO | WO 02/092503 A1 | 11/2002 | ............ C01B 21/064 |
| WO | WO 2004/052778 A2 | 6/2004 | ............ C01B 13/28 |
| WO | WO 2006/079213 A1 | 8/2006 | ................ B01J 2/04 |
| WO | WO-2008/130451 A2 | 10/2008 | |

OTHER PUBLICATIONS

Dr. Heike Mühlenweg et al., "Gas-Phase Reactions—Open Up New Roads to Nanoproducts", Degussa ScienceNewsletter No. 08, 2004, pp. 12-16.

H. Konrad et al., "Nanostructured Cu—Bi Alloys Prepared by Co-Evaporation in a Continuous Gas Flow," NanoStructured Materials, vol. 7, No. 6, 1996, pp. 605-610.

Kenvin et al. "Supported Catalysts Prepared from Mononuclear Copper Complexes: Catalytic Properties", Journal of Catalysis, pp. 81-91, (1992).

J. Heberlein, "New Approaches in Thermal Plasma Technology", Pure Appl. Chem., vol. 74, No. 3, 2002, pp. 327-335.

M.Vardelle et al., "Experimental Investigation of Powder Vaporization in Thermal Plasma Jets," Plasma Chemistry and Plasma Processing, vol. 11, No. 2, Jun. 1991, pp. 185-201.

National Aeronautics and Space Administration, "Enthalpy", http://www.grc.nasa.gov/WWW/K-12/airplane/enthalpy.html, Nov. 23, 2009, 1 page.

P. Fauchais et al., "Plasma Spray: Study of the Coating Generation," Ceramics International, Elsevier, Amsterdam, NL, vol. 22, No. 4, Jan. 1996, pp. 295-303.

P. Fauchais et al, "La Projection Par Plasma: Une Revue," Annales De Physique, vol. 14, No. 3, Jun. 1989, pp. 261-310.

T. Yoshida, "The Future of Thermal Plasma Processing for Coating", Pure & Appl. Chem., vol. 66, No. 6, 1994 pp. 1223-1230.

Hanet al., "Deformation Mechanisms and Ductility of Nanostructured Al Alloys", Mat. Res. Soc. Symp. Proc. vol. 821, Jan. 2004, Material Research Society, http://www.mrs.org/s_mrs/bin.asp?CID=2670&DOC=FILE.PDF., 6 pages.

Derwent English Abstract for publication No. SU 193241 A, Application No. 1973SU1943286 filed on Jul. 2, 1973, published on Mar. 1, 1976, entitled "Catalyst for Ammonia Synthesis Contains Oxides of Aluminium, Potassium, Calcium, Iron and Nickel Oxide for Increased Activity," 3 pgs.

Fauchais, P. et al. (Jan. 1993). "Les Dépôts Par Plasma Thermique," *Revue Générale De L'Electricité*, RGE, Paris, France, No. 2, pp. 7-12 with English machine translation.

Nagai, Y. et al. (Jul. 3, 2006). "Sintering Inhibition Mechanism of Platinum Supported on Ceria-Based Oxide and Pt-Oxide-Support Interaction," *J. Catalysis* 242:103-109.

Stiles, A. B. (Jan. 1, 1987). "Manufacture of Carbon-Supported Metal Catalysts," in *Catalyst Supports and Supported Catalysts*, Butterworth Publishers, MA, pp. 125-132.

Vardelle, A. et al. (1996). "Coating Generation: Vaporization of Particles in Plasma Spraying and Splat Formation," Universite de Limoges, 123 Avenue A. Thomas 87000, Limoges, France, *Pure & Chem. Appl.* 68(5):1093-1099.

Bateman, J. E. et al. (Dec. 17, 1998). "Alkylation of Porous Silicon by Direct Reaction with Alkenes and Alkynes," *Angew. Chem Int. Ed.* 37(19):2683-2685.

Carrot, G. et al. (Sep. 17, 2002). "Surface-Initiated Ring-Opening Polymerization: A Versatile Method for Nanoparticle Ordering," *Macromolecules* 35(22):8400-8404.

Chen, H.-S. et al. (Jul. 3, 2001). "On the Photoluminescence of Si Nanoparticles," *Mater. Phys. Mech.* 4:62-66.

Fojtik, A. et al. (Apr. 29, 1994). "Luminescent Colloidal Silicon Particles," *Chemical Physics Letters* 221:363-367.

Fojtik, A. (Jan. 13, 2006). "Surface Chemistry of Luminescent Colloidal Silicon Nanoparticles," *J. Phys. Chem. B.* 110(5):1994-1998.

Hua, F. et al. (Mar. 2006). "Organically Capped Silicon Nanoparticles With Blue Photoluminescence Prepared by Hydrosilylation Followed by Oxidation," *Langmuir* 22(9):4363-4370.

Jouet, R. J. et al. (Jan. 25, 2005). "Surface Passivation of Bare Aluminum Nanoparticles Using Perfluoroalkyl Carboxylic Acids," *Chem. Mater*.17(11):2987-2996.

Kim, N. Y. et al. (Mar. 5, 1997). "Thermal Derivatization of Porous Silicon with Alcohols," *J. Am. Chem. Soc.* 119(9):2297-2298.

Kwon, Y.-S. et al. (Apr. 30, 2003). "Passivation Process for Superfine Aluminum Powders Obtained by Electrical Explosion of Wires," *Applied Surface Science* 211:57-67.

Langner, A. et al. (Aug. 25, 2005). "Controlled Silicon Surface Functionalization by Alkene Hydrosilylation," *J. Am. Chem. Soc.* 127(37):12798-12799.

Li, D. et al. (Apr. 9, 2005). "Environmentally Responsive "Hairy" Nanoparticles: Mixed Homopolymer Brushes on Silica Nanoparticles Synthesized by Living Radical Polymerization Techniques," *J. Am. Chem. Soc.* 127(7):6248-6256.

Li, X. et al. (May 25, 2004). "Surface Functionalization of Silicon Nanoparticles Produced by Laser-Driven Pyrolysis of Silane Followed by HF—$HNO_3$ Etching," *Langmuir* 20(11):4720-4727.

Liao, Y.-C. et al. (Jun. 27, 2006). "Self-Assembly of Organic Monolayers on Aerosolized Silicon Nanoparticles," *J.Am. Chem. Soc.* 128(28):9061-9065.

Liu, S.-M. et al. (Jan. 13, 2006). "Enhanced Photoluminescence from Si Nano-Organosols by Functionalization With Alkenes and Their Size Evolution," *Chem. Mater.* 18(3):637-642.

Neiner, D. (Aug. 5, 2006). "Low-Temperature Solution Route to Macroscopic Amounts of Hydrogen Terminated Silicon Nanoparticles," *J. Am. Chem. Soc.* 128:11016-11017.

Netzer, L. et al. (1983). "A New Approach to Construction of Artificial Monolayer Assemblies," *J. Am. Chem. Soc.* 105(3):674-676.

"Platinum Group Metals: Annual Review 1996" (Oct. 1997). Engineering and Mining Journal, p. 63.

Sailor, M. J. (1997). "Surface Chemistry of Luminescent Silicon Nanocrystallites," *Adv. Mater.* 9(10):783-793.

Tao, Y.-T. (May 1993). "Structural Comparison of Self-Assembled Monolayers of n-Alkanoic Acids on the surfaces of Silver, Copper, and Aluminum," *J. Am. Chem. Soc.* 115(10):4350-4358.

Zou, J. et al. (Jun. 4, 2004). "Solution Synthesis of Ultrastable Luminescent Siloxane-Coated Silicon Nanoparticles," *Nano Letters* 4(7):1181-1186.

U.S. Appl. No. 13/291,983, filed Nov. 8, 2011, for Layman et al.
U.S. Appl. No. 12/152,084, filed May 9, 2008, for Biberger.
U.S. Appl. No. 13/028,693, filed Feb. 16, 2011, for Biberger.
U.S. Appl. No. 12/943,909, filed Nov. 10, 2010, for Layman.
U.S. Appl. No. 12/152,111, filed May 9, 2008, for Biberger et al.
U.S. Appl. No. 12/151,830, filed May 8, 2008, for Biberger et al.
U.S. Appl. No. 12/968,248, filed Dec. 14, 2010, for Biberger.
U.S. Appl. No. 12/968,245, filed Dec. 14, 2010, for Biberger.
U.S. Appl. No. 12/968,241, filed Dec. 14, 2010, for Biberger.
U.S. Appl. No. 12/968,239, filed Dec. 14, 2010, for Biberger.
U.S. Appl. No. 12/969,128, filed Dec. 15, 2010, for Biberger.
U.S. Appl. No. 12/962,463, filed Dec. 7, 2010, for Leaman.
U.S. Appl. No. 12/961,030, filed Dec. 6, 2010, for Lehman.
U.S. Appl. No. 12/961,108, filed Dec. 6, 2010, for Lehman.
U.S. Appl. No. 12/961,200, filed Dec. 6, 2010, for Lehman.
U.S. Appl. No. 12/968,253, filed Dec. 14, 2010, for Biberger.
U.S. Appl. No. 12/968,235, filed Dec. 14, 2010, for Biberger.
U.S. Appl. No. 12/969,306, filed Dec. 15, 2010, for Lehman et al.
U.S. Appl. No. 12/969,447, filed Dec. 15, 2010, for Biberger et al.
U.S. Appl. No. 12/969,087, filed Dec. 15, 2010, for Biberger.
U.S. Appl. No. 12/962,533, filed Dec. 7, 2010, for Yin et al.
U.S. Appl. No. 12/962,523, filed Dec. 7, 2010, for Yin et al.
U.S. Appl. No. 12/001,643, filed Dec. 11, 2007, for Biberger et al.
U.S. Appl. No. 12/474,081, filed May 28, 2009, for Biberger et al.
U.S. Appl. No. 12/001,602, filed Dec. 11, 2007, for Biberger et al.
U.S. Appl. No. 12/001,644, filed Dec. 11, 2007, for Biberger et al.
U.S. Appl. No. 12/969,457, filed Nov. 15, 2010, for Leamon et al.
U.S. Appl. No. 12/969,503, filed Nov. 15, 2010, for Leamon et al.
U.S. Appl. No. 12/954,813, filed Nov. 26, 2010, for Biberger.
U.S. Appl. No. 12/954,822, filed Nov. 26, 2010, for Biberger.
U.S. Appl. No. 13/033,514, filed Feb. 23, 2011, for Biberger et al.

* cited by examiner

GAS DELIVERY SYSTEM WITH CONSTANT OVERPRESSURE RELATIVE TO AMBIENT TO SYSTEM WITH VARYING VACUUM SUCTION

CROSS-REFERENCE TO RELATED APPLICATIONS

The present application is a divisional application claiming the benefit of priority from co-pending U.S. patent application Ser. No. 12/152,097, filed on May 9, 2008, entitled, "GAS DELIVERY SYSTEM WITH CONSTANT OVERPRESSURE RELATIVE TO AMBIENT TO SYSTEM WITH VARYING VACUUM SUCTION" and to U.S. Provisional Application Ser. No. 60/928,946, filed May 11, 2007, entitled "MATERIAL PRODUCTION SYSTEM AND METHOD," both of which are hereby incorporated by reference as if set forth herein. The co-pending U.S. patent application Ser. No. 11/110,341, filed on Apr. 10, 2005, entitled, "HIGH THROUGHPUT DISCOVERY OF MATERIALS THROUGH VAPOR PHASE SYNTHESIS" is incorporated by reference.

FIELD OF THE INVENTION

The present invention relates to systems for and methods of providing a constant overpressure gas to a system with varying internal pressure.

BACKGROUND OF THE INVENTION

Some particle production systems rely on vacuum suction forces to carry particle-containing mixtures from a reactor region to a collection region. However, when using such systems, care must be taken to produce or condition sensitive or reactive materials.

When operating in an ambient pressure environment, contamination may occur if the internal pressure of the system falls below the ambient pressure. One solution that can be effective is to seal the system. However, completely airtight seals, if available, are very expensive.

Often, less costly seals can be used if pressure within the system is maintained at a level above the ambient pressure. However, too large a differential between the system pressure and the ambient pressure can encourage leakage out of the system, which is also undesirable. Thus, the pressure differential should be minimized.

Unfortunately, in systems where the vacuum suction used is not constant, providing a fixed overpressure into the system will not effectively minimize the pressure differential between the system pressure and the ambient pressure.

What is needed is a system and a method capable of sufficiently minimizing the pressure differential in a system having a varying vacuum suction.

SUMMARY OF THE INVENTION

In one aspect of the present invention, a system operating in an environment having an ambient pressure is provided. The system comprises a reactor, a supply chamber, a suction generator, a conditioning fluid supply module, and a pressure regulation module. The reactor has a working gas inlet, a conditioning fluid inlet, a powder supply port, and a mixture outlet. The reactor is configured to receive a working gas through the working gas inlet, energize the working gas to form a plasma stream, receive powder particles through the powder supply port, receive the conditioning fluid through the conditioning fluid inlet, combine the plasma stream, the powder particles and the conditioning fluid, thereby altering the powder particles and forming a mixture stream, and supply the mixture stream to the mixture outlet. The altered powder particles are entrained within the mixture stream. The supply chamber is in fluid communication with the reactor through the conditioning fluid inlet. The suction generator is fluidly coupled to the reactor and configured to generate a suction force at the mixture outlet of the reactor. The conditioning fluid supply module is configured to supply the conditioning fluid at an original pressure. The pressure regulation module is fluidly coupled between the conditioning fluid supply module and the supply chamber. The pressure regulation module is configured to: receive the conditioning fluid at the original pressure from the conditioning fluid supply module, reduce the pressure of the conditioning fluid from the original pressure to a selected pressure relative to the ambient pressure, wherein the pressure regulation module is configured to maintain the reduction of the conditioning fluid pressure to the same selected pressure regardless of any changes in the suction force at the mixture outlet of the reactor, and supply the conditioning fluid at the selected pressure to the supply chamber.

In another aspect of the present invention, a method of supplying an overpressure gas to a particle production reactor operating in an environment having an ambient pressure is provided. The reactor has a working gas inlet, a conditioning fluid inlet, a powder supply inlet, and a mixture outlet. A suction generator provides a varying suction at the mixture outlet of the particle production reactor. A pressure regulation module receives a conditioning fluid at an original pressure from a conditioning fluid supply module. The pressure regulation module reduces the pressure of the conditioning fluid from the original pressure to a selected pressure relative to the ambient pressure, wherein the pressure regulation module maintains the reduction of the conditioning fluid pressure to the same selected pressure regardless of any changes in the suction force at the mixture outlet of the reactor. A supply chamber receives the conditioning fluid at the selected pressure from the pressure regulation module, wherein the supply chamber is fluidly coupled to the conditioning fluid inlet of the particle production reactor. The particle production reactor receives a working gas through the working gas inlet. The particle production reactor energizes the working gas to form a plasma stream. The particle production reactor receives powder particles through the powder supply port. The particle production reactor receives the conditioning fluid from the supply chamber through the conditioning fluid inlet. The particle production chamber combining the plasma stream, the powder particles and the conditioning fluid, thereby altering the powder particles and forming a mixture stream. The altered powder particles are entrained within the mixture stream. The mixture stream flows to the mixture outlet of the particle production reactor.

In preferred embodiments, the conditioning fluid supply module comprises a conditioning fluid reservoir and an evaporator. The conditioning fluid reservoir stores the conditioning fluid as a liquid gas. The evaporator receives the conditioning fluid as a liquid gas from the conditioning fluid reservoir. The evaporator then evaporates the conditioning fluid to produce the conditioning fluid in gaseous form. The pressure regulation module receives the conditioning fluid from the evaporator at the original pressure in gaseous form.

In some embodiments, the conditioning fluid supply module comprises a first conditioning fluid reservoir, a second conditioning fluid reservoir, a mixing valve, and an evaporator. The first conditioning fluid reservoir stores a first conditioning fluid as a liquid gas. The second conditioning fluid reservoir stores a second conditioning fluid as a liquid gas. The mixing valve receives the first conditioning fluid as a liquid gas from the first conditioning fluid reservoir and the second conditioning fluid as a liquid gas from the second conditioning fluid reservoir. The mixing valve then mixes the first conditioning fluid and the second conditioning fluid to form the conditioning fluid as a liquid gas. The evaporator then receives the conditioning fluid as a liquid gas from the mixing valve and evaporates the conditioning fluid to produce the conditioning fluid in gaseous form. The pressure regulation module then receives the conditioning fluid from the evaporator at the original pressure in gaseous form.

Preferably, the pressure regulation module comprises a pressure regulator fluidly coupled between the conditioning fluid supply module and the supply chamber. In some embodiments, the pressure regulator is a diaphragm-based pressure regulator.

In preferred embodiments, the pressure regulation module further comprises a pressure relief module fluidly coupled between the pressure regulator and the supply chamber. The pressure relief module receives the conditioning fluid from the pressure regulator and vents a portion of the conditioning fluid to the environment, thereby reducing the pressure of the conditioning fluid prior to entry into the supply chamber.

The pressure regulation module preferably comprises a plurality of pressure regulators fluidly coupled in serial formation between the conditioning fluid supply module and the supply chamber. Each one of the plurality of pressure regulators can be a diaphragm-based pressure regulator. In preferred embodiments, the plurality of pressure regulators comprises a first pressure regulator, a second pressure regulator, and a third pressure regulator. The first pressure regulator receives the conditioning fluid from the conditioning fluid supply module at the original pressure and reduces the pressure of the conditioning fluid from the original pressure to a second pressure. The second pressure regulator receives the conditioning fluid from the first pressure regulator at the second pressure and reduces the pressure of the conditioning fluid from the second pressure to a third pressure. The third pressure regulator receives the conditioning fluid from the second pressure regulator at the third pressure and reduces the pressure of the conditioning fluid from the third pressure to a fourth pressure.

In preferred embodiments, the reactor comprises a plasma torch and a reaction chamber. The plasma torch comprises the working gas inlet and a plasma outlet. The reaction chamber is fluidly coupled to the plasma outlet and comprises the conditioning fluid inlet, the powder supply port and the mixture outlet. The plasma torch receives the working gas through the working gas inlet and energizes the working gas to form the plasma stream. The plasma torch then supplies the plasma stream to the plasma outlet. The reaction chamber receives the plasma stream through the plasma outlet, receives the powder particles through powder supply port, and receives the conditioning fluid through the conditioning fluid inlet. The reaction chamber combines the plasma stream, the powder particles and the conditioning fluid to form the mixture stream. The reaction chamber then supplies the mixture stream to the mixture outlet.

In preferred embodiments, a collection system is fluidly coupled between the mixture outlet of the reaction chamber and the suction generator. The collection system receives the mixture stream from the reaction chamber. The collection system then separates and collects the altered powder particles from the mixture stream. Preferably, the collection system is fluidly coupled to the pressure regulation module receives the conditioning fluid at the selected pressure from the pressure regulation module.

In some embodiments, the step of combining the plasma stream, the powder particles and the conditioning fluid to alter the powder particles and form the mixture stream comprises the steps of the particle production reactor vaporizing the powder particles with the plasma stream and the particle production chamber condensing the vaporized powder particles.

In some embodiments, the conditioning fluid is argon. Furthermore, the selected pressure at which the pressure regulation module provides the conditioning fluid is preferably equal to or less than 498 Pascals (2 inches of water) relative to the ambient pressure, sufficiently minimizing the pressure differential in the system, while still providing a constant overpressure regardless of any variation in suction force at the reactor outlet.

DETAILED DESCRIPTION OF THE INVENTION

Figure 1:
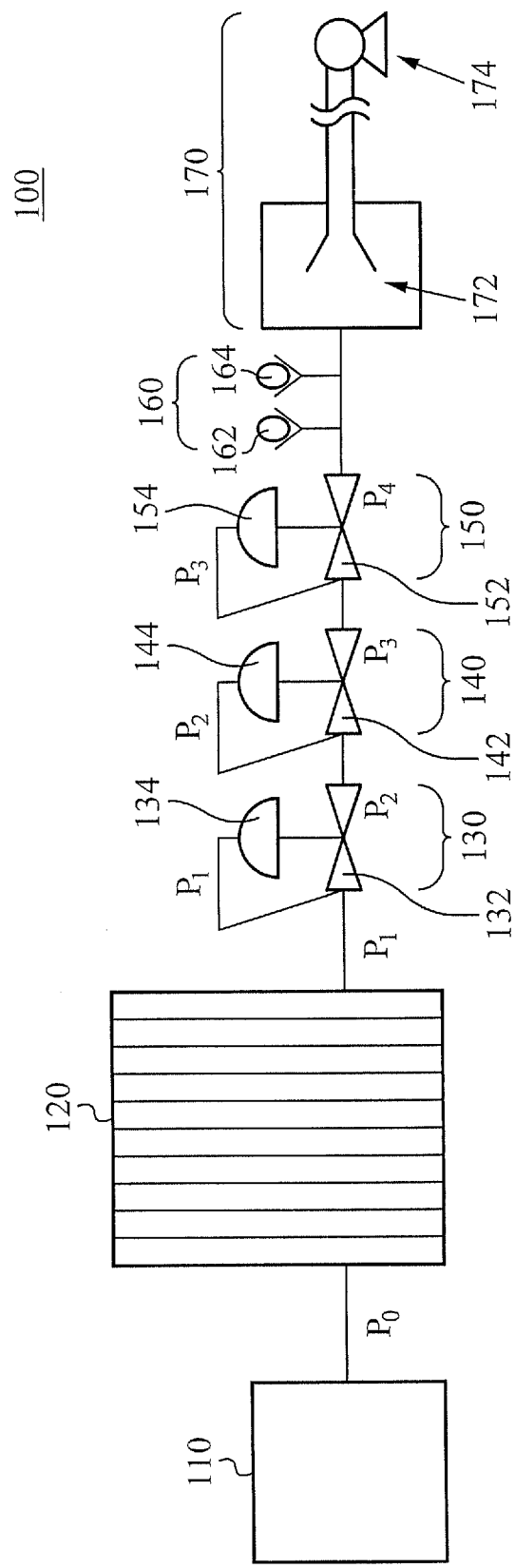
FIG. 1 is a schematic illustration of one embodiment of a gas supply system integrated into a particle production system with varying internal pressure in accordance with the principles of the present invention.

The description below concerns several embodiments of the invention. The discussion references the illustrated preferred embodiment. However, the scope of the present invention is not limited to either the illustrated embodiment, nor is it limited to those discussed, to the contrary, the scope should be interpreted as broadly as possible based on the language of the Claims section of this document.

In the following description, numerous details and alternatives are set forth for purpose of explanation. However, one of ordinary skill in the art will realize that the invention can be practiced without the use of these specific details. In other instances, well-known structures and devices are shown in block diagram form in order not to obscure the description of the invention with unnecessary detail.

This disclosure refers to both particles and powders. These two terms are equivalent, except for the caveat that a singular "powder" refers to a collection of particles. The present invention may apply to a wide variety of powders and particles. Powders that fall within the scope of the present invention may include, but are not limited to, any of the following: (a) nano-structured powders (nano-powders), having an average grain size less than 250 nanometers and an aspect ratio between one and one million; (b) submicron powders, having an average grain size less than 1 micron and an aspect ratio between one and one million; (c) ultra-fine powders, having an average grain size less than 100 microns and an aspect ratio between one and one million; and (d) fine powders, having an average grain size less than 500 microns and an aspect ratio between one and one million.

A wide variety of material types and forms can be processed in preferable particle production reactors used in the present invention. Without prejudice, the present invention specifically considers the provision of materials in the following forms: solid, liquid and gas.

An exemplary particle production system is a plasma powder production reactor, which is included within several of the exemplary embodiments discussed below. Generally, the plasma powder production reactor produces an output comprising particles entrained within a gas stream. Particle production preferably includes the steps of combination, reaction, and conditioning. The present invention can employ concepts similar to those used in the nano-powder production systems disclosed in related U.S. patent application Ser. No. 11/110,341, filed on Apr. 19, 2005 and entitled, "HIGH THROUGHPUT DISCOVERY OF MATERIALS THROUGH VAPOR PHASE SYNTHESIS", which is currently published as U.S. Publication No. 2005-0233380-A. In such nano-powder production systems, working gas is supplied from a gas source to a plasma reactor. Within the plasma reactor, energy is delivered to the working gas, thereby creating a plasma. A variety of different means can be employed to deliver this energy, including, but not limited to, DC coupling, capacitive coupling, inductive coupling, and resonant coupling. One or more material dispensing devices introduce at least one material, preferably in powder form, into the plasma reactor. The combination within the plasma reactor of the plasma and the material(s) introduced by the material dispensing device(s) forms a highly reactive and energetic mixture, wherein the powder can be vaporized. This mixture of vaporized powder moves through the plasma reactor in the flow direction of the working gas. As it moves, the mixture cools and particles are formed therein. The still-energetic output mixture, comprising hot gas and energetic particles, is emitted from the plasma reactor.

Referring now to FIG. 1, a gas supply system 100 is configured to deliver gas to a particle production (or processing) system 170 having varying internal pressure. The particle production system 170 includes a supply chamber 172 that is fluidly coupled to a suction generator 174, such as a vacuum pump, preferably through a conduit.

In a preferred embodiment, the gas supply system 100 includes a fluid (preferably gas) reservoir 110 fluidly coupled to an evaporator 120, which is in turn fluidly coupled to a pressure regulation module. The pressure regulation module preferably comprises a plurality of pressure regulators. In FIG. 1, the pressure regulation module comprises pressure regulators 130, 140, and 150 fluidly coupled together in serial formation. The outlet of the pressure regulation module is fluidly coupled with the supply chamber 172. In a preferred embodiment, at least one of the pressure regulators 130, 140, and 150 uses a diaphragm-based regulation mechanism. Preferably, the diaphragm-based regulation mechanism comprises a diaphragm-based demand valve.

The pressure regulation module can further include a pressure relief module 160 fluidly coupled between the pressure regulators and the supply chamber 172. The pressure relief module 160 preferably includes pressure relief valves 162 and 164. Pressure relief valves 162 and 164 are each independently coupled between the outlet of the pressure regulators and an inlet of the supply chamber 172. The pressure relief module 160 is configured to vent gas to the ambient environment.

The pressure regulation module is configured to receive a fluid (preferably a gas) having an original pressure and to reduce the pressure of the fluid from the original pressure to a selected pressure relative to the ambient pressure. The pressure regulation module is configured to maintain the reduction of the fluid pressure to the selected pressure regardless of any changes in the suction force generated by the suction generator 174 so that the fluid is provided to the supply chamber 172 at that same selected pressure whether the suction force increases, decreases or stays the same.

In a preferred operation of the system 100, the fluid reservoir 110 supplies liquefied gas (such as liquid argon) at pressure $P_0$ (such as approximately 360 PSI) to the evaporator 120. The evaporator 120 evaporates the liquefied gas to form a gas at pressure $P_1$ (such as approximately 300 PSI), which it supplies to the pressure regulation module. The pressures $P_0$ and $P_1$ are selected by configuring the reservoir 110 and evaporator 120. Typically, these pressures are much higher than the ambient pressure in which the system 100 operates. However both $P_1$ and $P_0$ are typically not directly dependent on the ambient pressure.

The pressure regulation module reduces the gas pressure from $P_1$ to an outlet pressure $P_4$, which is set relative to ambient pressure. The pressure regulation module controls pressure of the gas supplied to the supply chamber 172 to have a fixed pressure relative to the ambient, regardless of demand. In some embodiments, the outlet pressure $P_4$ is a fixed amount greater than the ambient pressure. In some embodiments, the outlet pressure $P_4$ has a fixed ratio relative to the ambient pressure. Typically, the specific relationship between the ambient pressure and $P_4$ depends on the configuration of the pressure regulation module. Preferably, $P_4$ is set only a slight amount above ambient pressure. In a preferred embodiment, the pressure regulation module reduces the gas pressure to approximately equal to or less than 498 Pascals (2 inches of water) relative to the ambient pressure. Preferably, the pressure is reduced to approximately 249 Pascals (1 inch of water) relative to the atmospheric pressure.

The pressure relief module 160 receives gas at pressure $P_4$. If $P_4$ is above a selected threshold, the pressure relief module 160 vents gas to the ambient environment, reducing the inlet pressure to the supply chamber 172. Preferably, the threshold is selected to be relatively high compared to ambient, so that under normal operation the pressure relief module 160 is not activated. As mentioned above, the pressure relief module 160 preferably comprises a plurality of pressure relief valves. As illustrated, the pressure relief module 160 includes a first pressure relief valve 162 and a second pressure relief valve 164. In some embodiments, the first pressure relief valve 162 and the second pressure relief valve 164 have differing sensitivities and are set at differing thresholds.

Referring back to the preferred operation, the first pressure regulator 130 receives the gas from the evaporator 120 at the inlet pressure $P_1$ (such as approximately 300 PSI) and outputs the gas at a reduced outlet pressure $P_2$ (such as approximately 50 PSI). Typically, the first pressure regulator 130 includes a control portion 134 and a valve portion 132. Control portion 134 uses input from $P_1$ and/or ambient pressure in determining the outlet pressure $P_2$.

The second pressure regulator 140 receives gas at the outlet pressure $P_2$ from the first pressure regulator 130 and outputs gas at a reduced outlet pressure $P_3$ (such as approximately 2 PSI). Typically, the second pressure regulator 140 includes a control portion 144 and a valve portion 142. Control portion 144 uses input from $P_2$ and/or ambient pressure in determining the outlet pressure $P_3$.

The third pressure regulator 150 receives gas at the outlet pressure $P_3$ from the second pressure regulator 140 and outputs gas at a reduced outlet pressure $P_4$ (such as approximately 249 Pascals (1 inch of water) relative to ambient pressure). Typically, the third pressure regulator 150 includes a control portion 154 and a valve portion 152. Control portion 154 uses input from $P_3$ and/or ambient pressure in determining the outlet pressure $P_4$.

In accordance with the present invention, embodiments of supply systems such as the one above are integrated into a variety of particle production or processing systems having varying vacuum loads. Some embodiments of the systems contemplated within the present invention are described below with reference to FIGS. 2 and 3.

Figure 2:
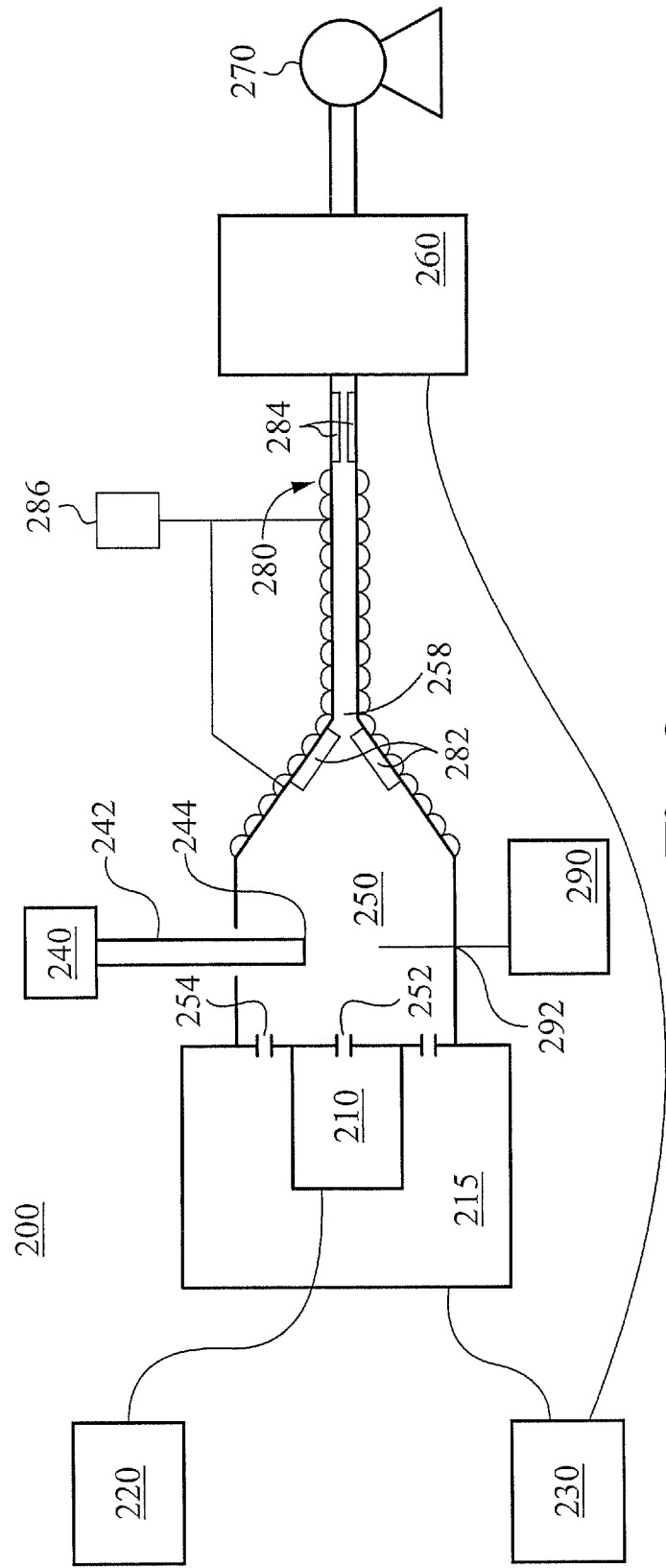
FIG. 2 is a schematic illustration of one embodiment of a particle processing system supplied by a gas delivery system in accordance with the principles of the present invention.

Referring now to FIG. 2, an embodiment of a powder processing apparatus 200 is presented. The powder processing apparatus 200 includes a plasma torch 210, a gas supply chamber 215, a reaction chamber 250, a powder dispensing device 240, a conditioning gas supply system 230, a working gas supply system 220, a collection system 260, and a suction generator 270.

The plasma torch 210 is configured to receive a working gas from the working gas supply system 220. Preferably, the working gas consists of impurity-binding atoms and noble gas atoms in a selectable ratio. During operation, the plasma torch 210 forms plasma from the working gas, preferably by delivering energy to the working gas.

The reaction chamber 250 defines a path from its input port 252 to its output port 258. The input port 252 is coupled with the plasma torch 210 and the output port 258 is coupled with the conduit system 280. Preferably, the plasma torch 210 is configured to deliver plasma into the reaction chamber 250 through the input port 252. In a preferred embodiment, the reaction chamber 250 comprises a substantially cylindrical portion extending away from the plasma torch 210 and into a frusto-conical portion, which comprises a wide end leading into a narrow end as it extends away from the plasma torch and into the output port 258. The wide end of the reaction chamber 250 preferably has an annular surface on which the input port 252 is disposed. The annular surface preferably has a large diameter relative to the size of the input port 252 through which the plasma stream enters the reaction chamber 250 from the plasma torch 210, thereby providing accommodation for the expansion of the plasma stream that occurs after the plasma stream flows into the reaction chamber 250. In a preferred embodiment, the frusto-conical surface is sufficiently smoothly varying so as to not unduly compress fluid flowing through the reaction chamber 250 to the output port 258.

The powder-dispensing device 240 is fluidly coupled with the reaction chamber 250 through a supply channel 242 and a supply port 244. The powder-dispensing device 240 can supply powder through the supply channel 242 to the supply port 244 and into the reaction chamber 250 at a selectable rate. Preferably, the supply channel 242 is configurable to deliver powder to a selectable location within the reaction chamber 250.

In a preferred embodiment, the reaction chamber 250 is fluidly coupled to the collection system 260 and the suction generator 270 via the conduit system 280. The suction generator 270 is configured to generate a suction force at the output port 258. The conduit system 280 is configured to receive a mixture stream from the reaction chamber 250 through the output port 258.

The gas supply chamber 215 is fluidly coupled to the reaction chamber 250, preferably through one or more inlets 254. In this respect, the gas supply chamber 215 can supply a fluid, such as a conditioning fluid, into the reaction chamber 250.

The conditioning gas supply system 230 is configured to deliver conditioning gas into the gas supply chamber 215 and to the collection system 260 at a selected pressure relative to ambient. In this respect, the conditioning gas supply system 230 can incorporate the pressure regulation module discussed above, as well as the fluid reservoir and the evaporator. As previously mentioned, the gas supply chamber 215 is fluidly coupled to the reaction chamber 250 and the collection system 260 is fluidly coupled to the conduit system 280. Preferably, the conditioning gas supply system 230 supplies conditioning gas to both the reaction chamber 250 and the collection system 260 at a constant pressure relative to ambient regardless of the demand from the suction generator 270. Alternatively, a separate, but similar, conditioning gas supply system supplies conditioning gas to the collection system 260. In the alternative embodiment, the two conditioning gas supply systems preferably supply the same pressure and contain the same type of conditioning gas. However, either the overpressure or the type of the gas supplied can vary between the two conditioning gas supply systems. The apparatus 200 can further comprise a reducing gas supply system 290 fluidly coupled through a gas supply port 292 into the reaction chamber 250.

Additionally, the apparatus 200 can comprise getter pumps 282 and 284, respectively configured at the output port 258 of the reaction chamber 250 and within the conduit 280 proximate to the collection system 260. Furthermore, the apparatus 200 can also comprise a temperature control system 286 that is coupled to a portion of the conduit system 280 and/or to a portion of the reaction chamber 250 and that is configured to control the temperature of the portion of the conduit system 280 and/or the reaction chamber 250.

In a preferred operation of the apparatus 200, the plasma torch 210 receives a working gas, such as a mixture of hydrogen and argon, from the working gas supply system 220 and delivers energy to the working gas, thereby forming a plasma stream. The suction generator 270 generates a suction force at the output port 258. The reaction chamber 250 receives powder from the powder dispensing device 240, conditioning gas from the conditioning gas supply system 230 through the supply chamber 215, and the plasma stream from the plasma torch 210. As discussed above, the pressure regulation module of the conditioning gas supply system 230 provides the conditioning gas to the supply chamber 215 at a selected pressure (preferably slightly above ambient pressure) regardless of any variation in the suction force at the output port 258.

The powder, conditioning gas, and the plasma stream mix within the reaction chamber, preferably altering the powder and forming a mixture stream within the reaction chamber 250. The mixture stream preferably comprises the altered powder entrained within the mixture stream. The mixture stream is forced through the output port 258 and through the collection system 260 by the suction generator 270.

The reducing gas supply system 290 preferably supplies reducing gas into the reaction chamber 250 through the supply channel 292. Preferably, the supply channel 292 is moveable to deliver reducing gas to a selectable location within the reaction chamber 250. Furthermore, the reducing gas supply system 290 preferably supplies reducing gas at a selectable rate. During operation, the reducing gas serves to flood a selectable portion of the reaction chamber 250 with reducing gas, to promote reduction and cool material within that region. For example, a location corresponding to a particular portion of a plasma plume can be flooded to take advantage of high temperatures that permit fast reduction reactions.

The getter pumps 282 and 284 are positioned to absorb impurities liberated from the powder during processing and prevent them from being reincorporated into the powder during cooling. During operation, as a powder is introduced into the reaction chamber 250, its particles encounter hot gasses and plasmas. The heating of the powder separates certain impurities from the particles of the powder. These impurities can remain separated, or later recombine as the particles and the gas cool. The getter pumps 282 are positioned to retain these impurities and prevent them from reuniting with the particles of the powder. Farther along in the conduit system 280, the getter pumps 284 are positioned to retain the liberated impurities and any other impurities that may form during the cooling of the mixture as it moves from the reaction chamber 250 through the conduit system 280.

The temperature control system 286 is configured to control the temperature of the walls of the conduit system 280 between the reaction chamber 250 and the collection system 260. Furthermore, the temperature control system 286 can also control the temperature of some of the walls of the reaction chamber 250. Preferably, the temperature of the walls is controlled to minimize contamination of the conduit system 280 and of the reaction chamber 250 (e.g., particle deposition). In an alternative embodiment, the interior surface of the conduit system 280 is coated to minimize contamination. Of course, it is contemplated that coatings and temperature control can be used in concert.

The mixture stream preferably flows from the conduit system 280 through the collection system 260. The collection system 260 separates and collects powder particles from the mixture stream, allowing rest of the mixture stream to flow through towards the suction generator 270. The collection system 260 preferably permits the suction generator 270 to provide a motive force there-through. However, in some embodiments the collection system 260 provides additional motive force. The collection system 260 is preferably configured to separate a portion of the particles transported within the mixture stream from the main body of the stream and to allow removal and analysis of the particles. Furthermore, the collection system 260 can take multiple samples, at selected times, and can sample discontinuously, which allows for sampling from gas-particle streams whose composition may vary from time to time without contamination from previous product.

It is contemplated that the collection system 260 can be configured in a variety of ways. In one embodiment, the collection system 260 comprises a sampling structure, at least one filled aperture formed in the sampling structure, and at least one unfilled aperture formed in the sampling structure. Each filled aperture is configured to collect particles from the mixture stream, such as by using a filter. The sampling structure is configured to be adjusted between a pass-through configuration and a collection configuration. The pass-through configuration comprises an unfilled aperture being fluidly aligned with a conduit, such as the conduit system 280, thereby allowing the unfilled aperture to receive the mixture stream from the conduit and the mixture stream to flow through the sampling structure without substantially altering the particle content of the mixture stream. The collection configuration comprises a filled aperture being fluidly aligned with the conduit, thereby allowing the filled aperture to receive the mixture stream and collect particles while the mixture stream is being flown through the filled aperture.

It is contemplated that the sampling structure can be adjusted between the pass-through configuration and the collection configuration in a variety of ways. In one embodiment, the sampling structure is a disk-shaped structure including an annular array of apertures, wherein the annular array comprises a plurality of the filled apertures and a plurality of the unfilled apertures. The sampling structure is rotatably mounted to a base, wherein rotational movement of the sampling structure results in the adjustment of the sampling structure between the pass-through configuration and the collection configuration. In another embodiment, the sampling structure is a rectangular-shaped structure including a linear array of apertures, wherein the linear array comprises a plurality of the filled apertures and a plurality of the unfilled apertures. The sampling structure is slideably mounted to a base, wherein sliding of the sampling structure results in the adjustment of the sampling structure between the pass-through configuration and the collection configuration.

Figure 3:
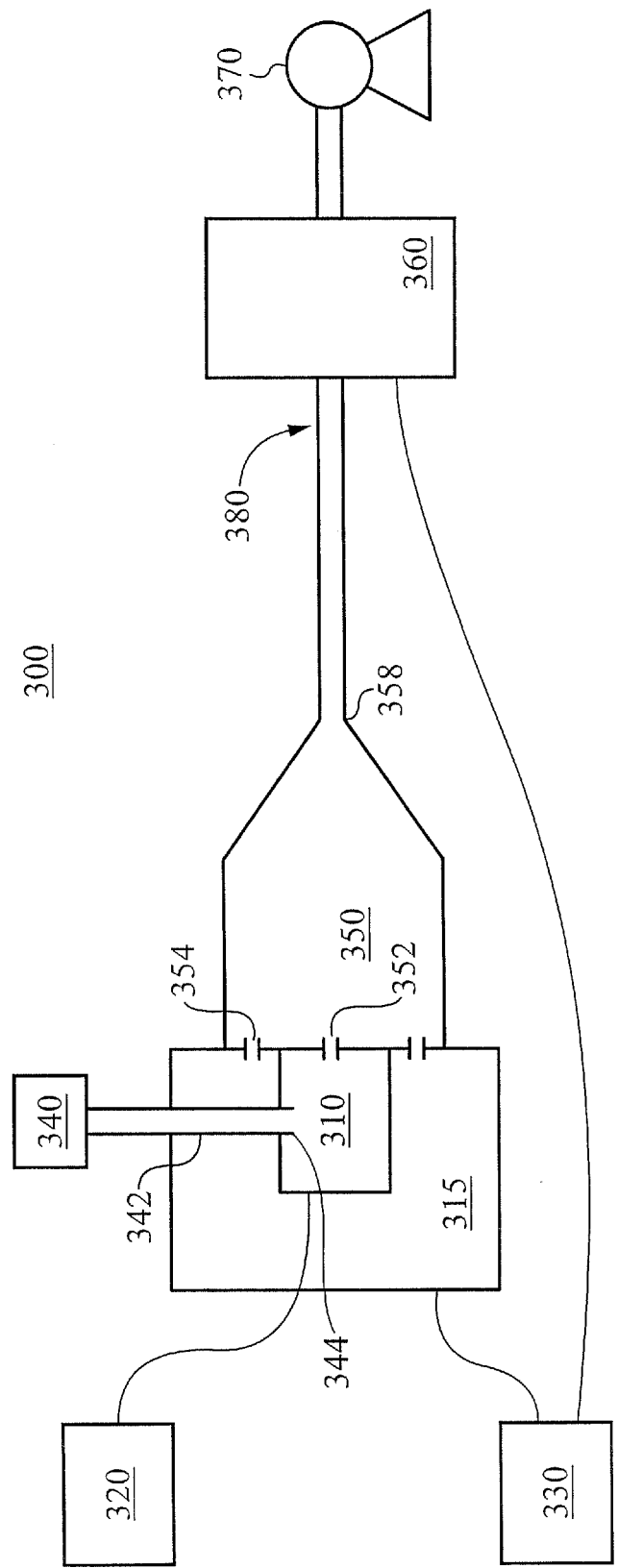
FIG. 3 is a schematic illustration of one embodiment of a particle production system supplied by a gas delivery system in accordance with the principles of the present invention.

FIG. 3 is a schematic illustration of one embodiment of a particle production system 300 supplied by a gas delivery system in accordance with the principles of the present invention. The powder production system 300 is similar to the system 200 of FIG. 2 and includes a plasma torch 310, a gas supply chamber 315, a reaction chamber 350, a powder dispensing device 340, a conditioning gas supply system 330, a working gas supply system 320, a collection system 360, and a suction generator 370.

The plasma torch 310 is configured to receive a working gas from the working gas supply system 320. Preferably, the working gas consists of impurity-binding atoms and noble gas atoms in a selectable ratio. During operation, the plasma torch 310 forms plasma from the working gas, preferably by delivering energy to the working gas.

The reaction chamber 350 defines a path from its input port 352 to its output port 358. The input port 352 is coupled with the plasma torch 310 and the output port 358 is coupled with the conduit system 380. Preferably, the plasma torch 310 is configured to deliver plasma into the reaction chamber 350 through the input port 352. In a preferred embodiment, the reaction chamber 350 comprises a substantially cylindrical portion extending away from the plasma torch 310 and into a frusto-conical portion, which comprises a wide end leading into a narrow end as it extends away from the plasma torch and into the output port 358. The wide end of the reaction chamber 350 preferably has an annular surface on which the input port 352 is disposed. The annular surface preferably has a large diameter relative to the size of the input port 352 through which the plasma stream enters the reaction chamber 350 from the plasma torch 310, thereby providing accommodation for the expansion of the plasma stream that occurs after the plasma stream flows into the reaction chamber 350. In a preferred embodiment, the frusto-conical surface is sufficiently smoothly varying so as to not unduly compress fluid flowing through the reaction chamber 350 to the output port 358.

The powder-dispensing device 340 is fluidly coupled with the plasma torch 310 through a supply channel 342, thereby allowing the powder to flow into the plasma torch, as opposed to the powder flowing directly into the reaction chamber as in FIG. 2. The powder-dispensing device 340 can supply powder at a selectable rate. Preferably, the supply channel 342 is configurable to deliver powder to a selectable location within the plasma torch 310.

In a preferred embodiment, the reaction chamber 350 is fluidly coupled to the collection system 360 and the suction generator 370 via the conduit system 380. The suction generator 370 is configured to generate a suction force at the output port 358. The conduit system 380 is configured to receive a mixture stream from the reaction chamber 350 through the output port 358.

The gas supply chamber 315 is fluidly coupled to the reaction chamber 350, preferably through one or more inlets 354. In this respect, the gas supply chamber 315 can supply a fluid, such as a conditioning fluid, into the reaction chamber 350.

The conditioning gas supply system 330 is configured to deliver conditioning gas into the gas supply chamber 315 and to the collection system 360 at a selected pressure relative to ambient. In this respect, the conditioning gas supply system 330 can incorporate the pressure regulation module discussed above, as well as the fluid reservoir and the evaporator. As previously mentioned, the gas supply chamber 315 is fluidly coupled to the reaction chamber 350 and the collection system 360 is fluidly coupled to the conduit system 380. Preferably, the conditioning gas supply system 330 supplies conditioning gas to both the reaction chamber 350 and the collection system 360 at a constant pressure relative to ambient regardless of the demand from the suction generator 370. Alternatively, a separate, but similar, conditioning gas supply system supplies conditioning gas to the collection system 360. In the alternative embodiment, the two conditioning gas supply systems preferably supply the same pressure and contain the same type of conditioning gas. However, either the overpressure or the type of the gas supplied can vary between the two conditioning gas supply systems.

Additionally, the apparatus 300 can comprise getter pumps and/or a temperature control system, such as those discussed with respect to FIG. 2.

In a preferred operation of the system 300, the plasma torch 310 receives a working gas, such as a mixture of hydrogen and argon, from the working gas supply system 320 and receives powder from the powder dispensing device 340. The plasma torch 310 delivers energy to the working gas, thereby forming a plasma stream. The plasma stream is applied to the powder within the plasma torch, thereby altering the powder and forming a mixture stream within which the altered powder is entrained. In a preferred embodiment, the plasma stream vaporizes the powder.

The suction generator 370 generates a suction force at the output port 358. The reaction chamber 350 receives conditioning gas from the conditioning gas supply system 330 through the supply chamber 315, and the mixture stream from the plasma torch 310. As discussed above, the pressure regulation module of the conditioning gas supply system 330 provides the conditioning gas to the supply chamber 315 at a selected pressure (preferably slightly above ambient pressure) regardless of any variation in the suction force at the output port 358. Within the reaction chamber 350, the species within the mixture stream supplied from the plasma torch 310 condense to form particles.

The conditioning gas mixes with the mixture stream within the reaction chamber 350. In certain embodiments, the conditioning fluid serves to cool the mixture stream. The mixture stream is then forced through the output port 358 and through the collection system 360 to the collection system 360 by the suction generator 370. The collection system 360 can have all of the same features as collection system 260 discussed above with respect to FIG. 2.

Figure 4:
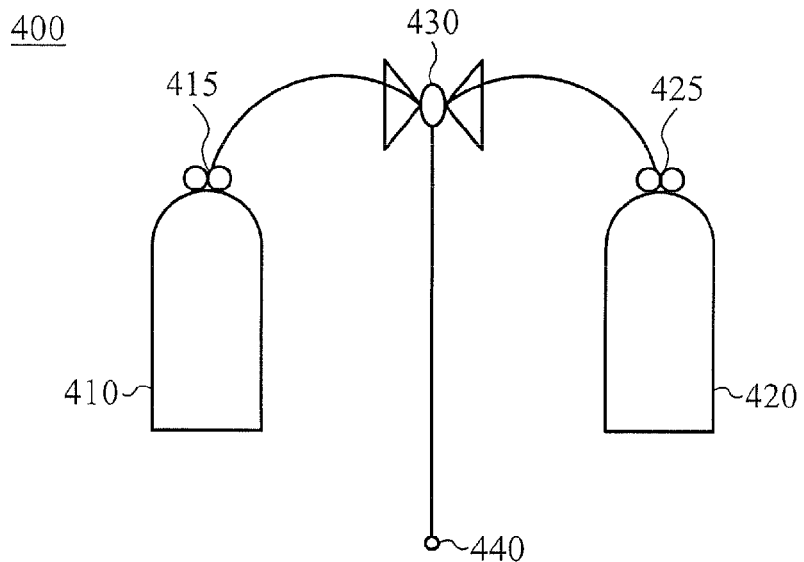
FIG. 4 is a schematic illustration of one embodiment of a gas reservoir for use in a powder processing system in accordance with the principles of the present invention.

Fluid reservoirs used within some embodiments of the present invention can be configured to supply a mixture of fluids. Referring now to FIG. 4, a mixed gas reservoir system 400 for use in the certain embodiments of the fluid supply systems of the present invention is discussed. The reservoir system 400 includes a first gas reservoir 410 containing a first gas and a second gas reservoir 420 containing a second gas.

The first gas reservoir 410 and the second gas reservoir 420 are fluidly coupled through regulators 415 and 425, respectively, to a mixing valve 430 and an output conduit 440. During operation, tuning of the regulators 415 and 425 along with the mixing valve 430 can produce a desired ratio of the first gas and the second gas. It is contemplated that these reservoirs can store and supply fluid in gaseous form or as a liquified gas.

Figure 5:
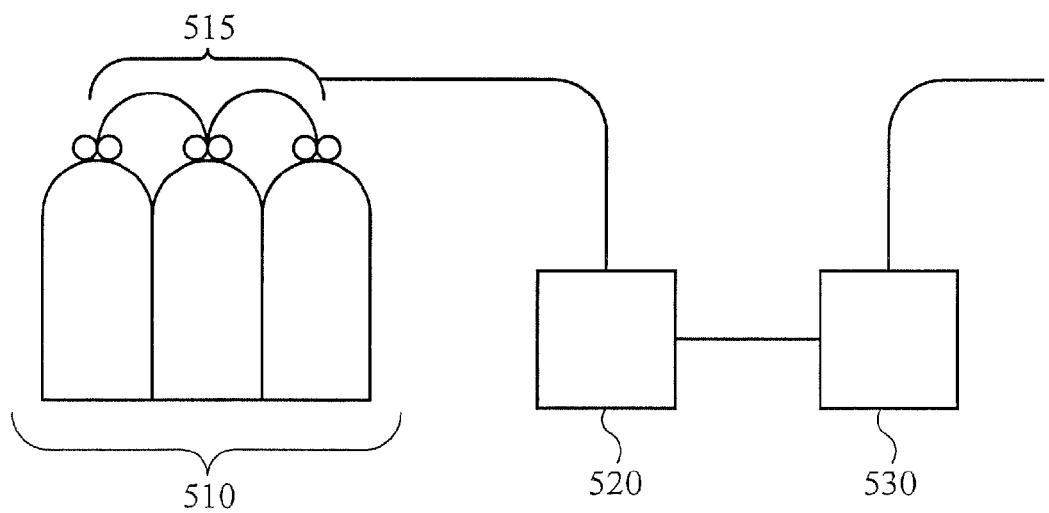
FIG. 5 is a schematic illustration of one embodiment of a conditioning gas supply system for use in a powder processing system in accordance with the principles of the present invention.

Referring now to FIG. 5, a conditioning gas supply system 500 is disclosed for use in a powder processing or production system, such as those discussed above. The conditioning gas supply system 500 is capable of supplying conditioning gas, whether in gaseous form or as a liquified gas, to a supply chamber at a substantially constant pressure relative to a range of different suction conditions within the chamber. The conditioning gas supply system 500 includes conditioning gas reservoirs 510 fluidly coupled through a manifold 515 to an evaporator 520, such as the evaporator 120 of FIG. 2. The evaporator 520 is fluidly coupled to a pressure regulation module 530, such as the pressure regulation module discussed with respect to FIG. 1. During operation, gas supplied from the reservoirs 510 through the manifold 515 is evaporated in the evaporator 520, and then passed through the pressure regulation module 530. The pressure regulated gas is then supplied from the pressure regulation module 530 into the supply chamber, where it can be used in a powder processing or production system as previously discussed. The pressure regulation module 530 controls the pressure of the gas supplied to the supply chamber, maintaining a fixed pressure relative to the ambient pressure, regardless of demand. In some embodiments, the system of FIG. 5 includes pressure regulation modules as outlined with respect to FIG. 1.

Figure 6:
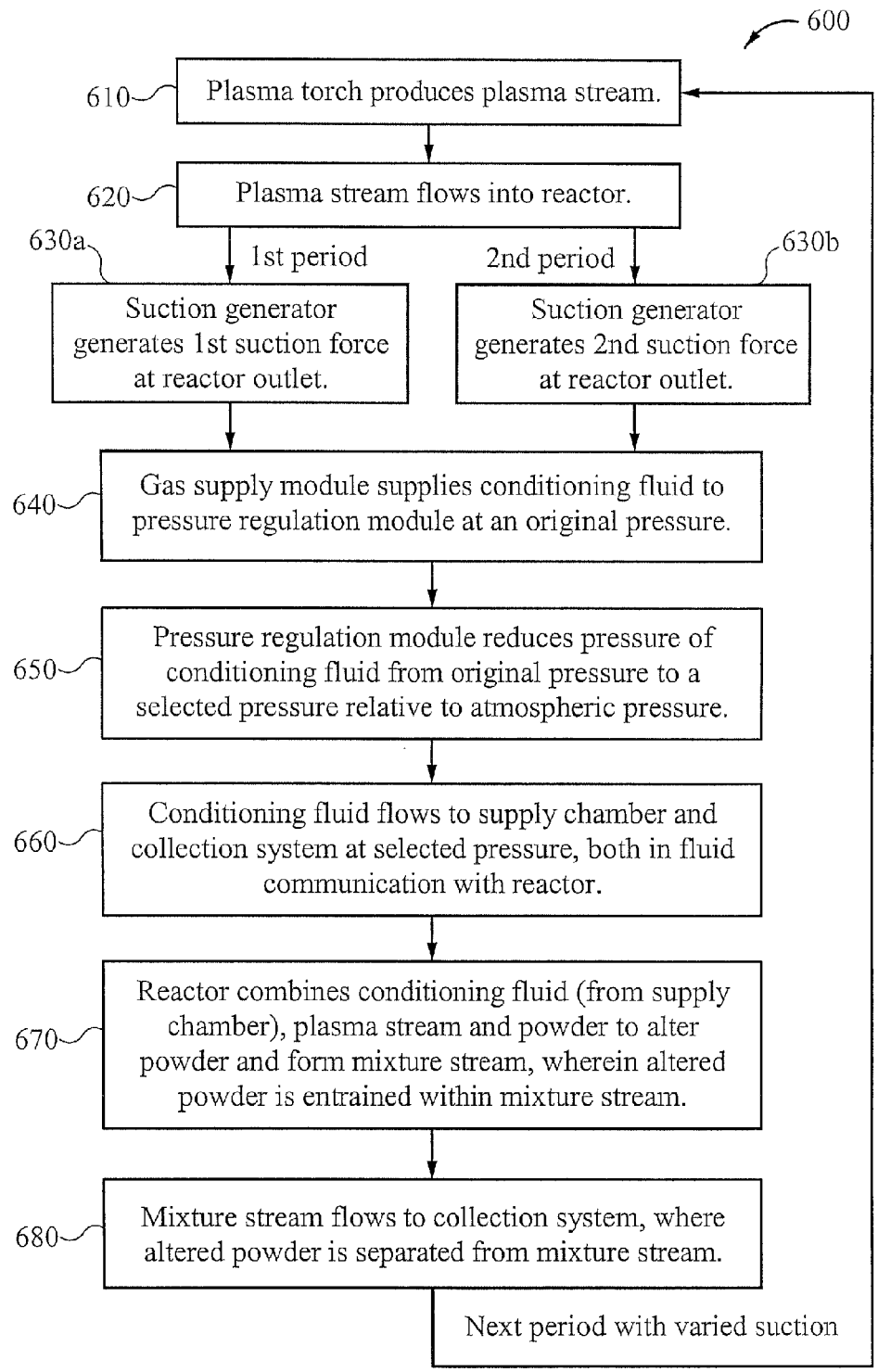
FIG. 6 is a flowchart illustrating one embodiment of a method of providing a constant overpressure gas to a system with varying internal pressure in accordance with the principles of the present invention.

FIG. 6 illustrates one embodiment of a method 600 of supplying an overpressure gas to a particle production system operating in an environment having an ambient pressure. The particle production system preferably comprises a plasma torch having a working gas inlet and a reactor chamber having a conditioning fluid inlet, a powder supply port, and a mixture outlet.

During a first period, the plasma torch produces a plasma stream at step 610. In a preferred embodiment, the plasma torch receives a working gas through the working gas inlet, then energizes the working gas to form the plasma stream. At step 620, the plasma stream flows into the reactor chamber. During the first period, a suction generator provides a first suction force at the mixture outlet of the reactor chamber at step 630a. At step 640, a gas supply module supplies conditioning fluid to a pressure regulation module at an original pressure. In one embodiment, the conditioning fluid is pure argon. At step 650, the pressure regulation module reduces the pressure of the conditioning fluid from the original pressure to a selected pressure relative to the atmospheric pressure. It is contemplated that the selected pressure can comprise a small range above the ambient pressure, such as equal to or less than approximately 498 Pascals (2 inches of water) over atmosphere, or can be a specific level, such as equal to approximately 249 Pascals (1 inch of water) over atmosphere. At step 660, the conditioning fluid flows from the pressure regulation module into the supply chamber, and optionally to a collection system fluidly coupled downstream from the reactor chamber, at the selected pressure. The supply chamber is fluidly coupled to the conditioning fluid inlet of the reactor chamber. At step 670, the reactor chamber combines the plasma stream from the plasma torch, powder particles from the powder supply port, and the conditioning fluid from the supply chamber, thereby altering the powder particles and forming a mixture stream. It is contemplated that the powder particles can be delivered into directly into the reactor chamber (as in FIG. 2) or can be first delivered into the plasma torch (as in FIG. 3). The altered powder particles are entrained within the mixture stream. At step 680, the mixture stream flows to the mixture outlet of the reactor chamber. It can then flow to the rest of the system, such as the collection system.

The pressure regulation module maintains the reduction of the conditioning fluid pressure to the same selected pressure regardless of any changes in the suction force at the mixture outlet of the reactor. In this respect, the process can repeat itself during another period defined by a varied suction force and perform the same steps. As seen in FIG. 6, instead of the suction generator providing a first suction force at step 630a, the suction generator provides a second suction force at step 630b. Although the second suction force it different from the first suction force, the pressure regulation module still regulates the pressure of the conditioning fluid and supplies the conditioning fluid to the supply chamber at the same selected pressure, preferably at 249-498 Pascals (1-2 inches of water) over atmosphere.

As would be appreciated by those of ordinary skill in the art, the protocols, processes, and procedures described herein may be repeated continuously or as often as necessary to satisfy the needs described herein. Additionally, although the operations are shown or described in a specific order, certain steps may occur simultaneously or in a different order than illustrated. For example, the reactor can receive the conditioning fluid before, during or after the period it receives the working gas and/or the powder. Accordingly, the operations of the present invention should not be limited to any particular order unless either explicitly or implicitly stated in the claims. In this respect, the use of letters as element headings (e.g., a), b), c), etc.) should not be interpreted as limiting the scope of a claim to any particular order other than that otherwise required by the actual claim language.

The present invention has been described in terms of specific embodiments incorporating details to facilitate the understanding of the principles of construction and operation of the invention. As such, references herein to specific embodiments and details thereof are not intended to limit the scope of the claims appended hereto. It will be apparent to those skilled in the art that modifications can be made to the embodiments chosen for illustration without departing from the spirit and scope of the invention.

What is claimed is:

1. A method of supplying an overpressure gas to a particle production reactor operating in an environment having an ambient pressure, the reactor having a working gas inlet, a conditioning fluid inlet, a powder supply port, and a mixture outlet, wherein the method comprises the steps of:

generating a suction force at the mixture outlet of the particle production reactor by a suction generator;

receiving, by a pressure regulation module, a conditioning fluid at an original pressure from a conditioning fluid supply module;

reducing, by the pressure regulation module, the pressure of the conditioning fluid from the original pressure to a selected pressure relative to the ambient pressure, wherein said selected pressure is above ambient pressure;

maintaining the reduction of the conditioning fluid pressure, by the pressure regulation module, to the same selected pressure relative to the ambient pressure regardless of any changes in the suction force at the mixture outlet of the reactor;

receiving the conditioning fluid at the selected pressure from the pressure regulation module, by a supply chamber fluidly coupled to the conditioning fluid inlet of the particle production reactor;

receiving a working gas through the working gas inlet, by the particle production reactor;

energizing the working gas by the particle production reactor, thereby forming a plasma stream;

receiving, by the particle production reactor, powder particles through the powder supply port;

receiving, by the particle production reactor, the conditioning fluid from the supply chamber through the conditioning fluid inlet;

combining the plasma stream, the powder particles and the conditioning fluid, by the particle production chamber, thereby altering the powder particles and forming a mixture stream, wherein the altered powder particles are entrained within the mixture stream; and flowing the mixture stream to the mixture outlet of the particle production reactor.

2. The method of claim 1, wherein the conditioning fluid supply module comprises a conditioning fluid reservoir and an evaporator, and the method further comprises the steps of:

storing the conditioning fluid as a liquid gas, by the conditioning fluid reservoir;

receiving the conditioning fluid as a liquid gas, by the evaporator, from the conditioning fluid reservoir;

evaporating the conditioning fluid, by the evaporator, to produce the conditioning fluid as a gas; and receiving the conditioning fluid as a gas, by the pressure regulation module, from the evaporator at the original pressure.

3. The method of claim 1, wherein the conditioning fluid supply module comprises a first conditioning fluid reservoir, a second conditioning fluid reservoir, a mixing valve, and an evaporator, and the method further comprises the steps of:

storing a first conditioning fluid as a liquid gas, by the first conditioning fluid reservoir;

storing a second conditioning fluid as a liquid gas, by the second conditioning fluid reservoir;

receiving, by the mixing valve, the first conditioning fluid as a liquid gas from the first conditioning fluid reservoir and receiving, by the mixing valve, the second conditioning fluid as a liquid gas from the second conditioning fluid reservoir;

mixing the first conditioning fluid and the second conditioning fluid, by the mixing valve, to form a conditioning fluid as a liquid gas;

receiving the conditioning fluid as a liquid gas, by the evaporator, from the mixing valve;

evaporating the conditioning fluid to produce the conditioning fluid as a gas, by the evaporator; and receiving the conditioning fluid as a gas, by the pressure regulation module, from the evaporator at the original pressure.

4. The method of claim 1, wherein the step of reducing the pressure of the conditioning fluid is performed by a pressure regulator fluidly coupled between the conditioning fluid supply module and the supply chamber.

5. The method of claim 4, wherein the step of maintaining the reduction of the conditioning fluid pressure is performed using a diaphragm-based pressure regulator.

6. The method of claim 4, wherein the pressure regulation module further comprises a pressure relief module fluidly coupled between the pressure regulator and the supply chamber, and the method further comprises the steps of:

receiving the conditioning fluid, by the pressure relief module, from the pressure regulator; and
reducing the pressure of the conditioning fluid prior to entry into the supply chamber, by the pressure relief module venting a portion of the conditioning fluid to the environment.

7. The method of claim 1, wherein the steps of reducing and maintaining the pressure of the conditional fluid are performed by a plurality of pressure regulators fluidly coupled in a serial formation between the conditioning fluid supply module and the supply chamber.

8. The method of claim 7, wherein each one of the plurality of pressure regulators is a diaphragm-based pressure regulator.

9. The method of claim 7, wherein the plurality of pressure regulators comprises a first pressure regulator, a second pressure regulator, and a third pressure regulator, and the method further comprises the steps of:
receiving the conditioning fluid from the conditioning fluid supply module at the original pressure, by the first pressure regulator;
reducing the pressure of the conditioning fluid from the original pressure to a second pressure, by the first pressure regulator;
receiving the conditioning fluid from the first pressure regulator at the second pressure, by the second pressure regulator;
reducing the pressure of the conditioning fluid from the second pressure to a third pressure, by the second pressure regulator;
receiving the conditioning fluid from the second pressure regulator at the third pressure, by the third pressure regulator; and
reducing the pressure of the conditioning fluid from the third pressure to a fourth pressure, by the third pressure regulator.

10. The method of claim 7, wherein the pressure regulation module further comprises a pressure relief module fluidly coupled between the plurality of pressure regulators and the supply chamber, and the method further comprises the steps of:
receiving the conditioning fluid downstream from the plurality of pressure regulators, by the pressure relief module; and
reducing the pressure of the conditioning fluid prior to entry into the supply chamber by the pressure relief module venting a portion of the conditioning fluid to the environment.

11. The method of claim 1, wherein the reactor comprises a plasma torch and a reaction chamber, the plasma torch comprising the working gas inlet and a plasma outlet, the reaction chamber fluidly coupled to the plasma outlet and comprising the conditioning fluid inlet, the powder supply port and the mixture outlet, and the method further comprises the steps of:
receiving the working gas through the working gas inlet, by the plasma torch;
energizing the working gas to form the plasma stream, by the plasma torch;
supplying the plasma stream to the plasma outlet, by the plasma torch;
receiving the plasma stream through the plasma outlet, by the reaction chamber;
receiving the powder particles through the powder supply port, by the reaction chamber;
receiving the conditioning fluid through the conditioning fluid inlet, by the reaction chamber;
combining the plasma stream, the powder particles and the conditioning fluid to form the mixture stream, by the reaction chamber;
supplying the mixture stream to the mixture outlet, by the reaction chamber.

12. The method of claim 11, wherein a collection system is fluidly coupled between the mixture outlet of the reaction chamber and the suction generator, and the method further comprises the steps of:
receiving the mixture stream from the reaction chamber, by the collection system; and
separating and collecting the altered powder particles from the mixture stream, by the collection system.

13. A method of supplying an overpressure gas to a particle production reactor operating in an environment having an ambient pressure, the reactor having a plasma torch and a reaction chamber, the plasma torch comprising a working gas inlet and a plasma outlet, the reaction chamber fluidly coupled to the plasma outlet and comprising a conditioning fluid inlet, a powder supply port, a mixture outlet, a collection system fluidly coupled between the mixture outlet of the reaction chamber and a suction generator, and the collection system is fluidly coupled to the pressure regulation module, and the method further comprises the steps of:
generating a suction force at the mixture outlet of the particle production reactor by the suction generator;
receiving, by a pressure regulation module, a conditioning fluid at an original pressure from a conditioning fluid supply module;
reducing, by the pressure regulation module, the pressure of the conditioning fluid from the original pressure to a selected pressure relative to the ambient pressure, wherein said selected pressure is above ambient pressure;
maintaining the reduction of the conditioning fluid pressure, by the pressure regulation module, to the same selected pressure relative to the ambient pressure regardless of any changes in the suction force at the mixture outlet of the reactor;
receiving the conditioning fluid at the selected pressure from the pressure regulation module, by a supply chamber fluidly coupled to the conditioning fluid inlet of the particle production reactor;
receiving the conditioning fluid, by the particle production reactor, from the supply chamber through the conditioning fluid inlet;
receiving a working gas through the working gas inlet, by the plasma torch;
energizing the working gas by the plasma torch, thereby forming a plasma stream;
supplying the plasma stream to the plasma outlet, by the plasma torch;
receiving the plasma stream through the plasma outlet, by the reaction chamber;
receiving, by the reaction chamber, powder particles through the powder supply port;
receiving, by the reaction chamber, the conditioning fluid from the reaction chamber through the conditioning fluid inlet;
combining the plasma stream, the powder particles and the conditioning fluid, by the reaction chamber, thereby altering the powder particles and forming a mixture stream, wherein the altered powder particles are entrained within the mixture stream;
flowing the mixture stream to the mixture outlet, by the reaction chamber;

receiving the mixture stream from the reaction chamber, by the collection system;

receiving the conditioning fluid at the selected pressure from the pressure regulation module, by the collection system; and separating and collecting the altered powder particles from the mixture stream, by the collection system.

14. The method of claim 1, wherein the step of combining the plasma stream, the powder particles and the conditioning fluid to alter the powder particles and form the mixture stream comprises the steps of:

vaporizing the powder particles with the plasma stream, by the particle production reactor, to form vaporized material; and cooling the vaporized material to form powder particles.

15. The method of claim 1, wherein the pressure regulation module comprises a first pressure regulator, a second pressure regulator, and a third pressure regulator, the conditioning fluid supply module comprises a conditioning fluid reservoir and an evaporator, and the method further comprises the steps of:

storing the conditioning fluid, by the conditioning fluid reservoir, wherein the conditioning fluid is liquid argon;

receiving the conditioning fluid from the conditioning fluid reservoir, by the evaporator;

evaporating the conditioning fluid to produce the conditioning fluid in gaseous form, by the evaporator;

receiving the conditioning fluid from the evaporator at the original pressure, by the first pressure regulator;

reducing the pressure of the conditioning fluid from the original pressure to a second pressure, by the first pressure regulator;

receiving the conditioning fluid from the first pressure regulator at the second pressure, by the second pressure regulator;

reducing the pressure of the conditioning fluid from the second pressure to a third pressure, by the second pressure regulator;

receiving the conditioning fluid from the second pressure regulator at the third pressure, by the second pressure regulator; and reducing the pressure of the conditioning fluid from the third pressure to a fourth pressure, by the third pressure regulator.

16. The method of claim 15, wherein the selected pressure is equal to or less than 498 Pascals (2 inches of water) relative to the ambient pressure.

17. A method of supplying an overpressure gas to a particle production reactor operating in an environment having an ambient pressure, a conditioning fluid inlet, a powder supply port, and a mixture outlet, wherein the method comprises the steps of:

generating a suction force at the mixture outlet of the particle production reactor, by a suction generator;

receiving, by a pressure regulation module, a conditioning fluid at an original pressure from a conditioning fluid supply module;

reducing, by the pressure regulation module, the pressure of the conditioning fluid from the original pressure to a selected pressure relative to the ambient pressure, wherein said selected pressure is above ambient pressure;

maintaining the reduction of the conditioning fluid pressure, by the pressure regulation module, to the same selected pressure relative to the ambient pressure regardless of any changes in the suction force at the mixture outlet of the reactor;

receiving the conditioning fluid at the selected pressure from the pressure regulation module, by a supply chamber fluidly coupled to the conditioning fluid inlet of the particle production reactor;

forming a plasma stream, by the particle production reactor;

receiving, by the particle production reactor, powder particles through the powder supply port;

receiving, by the particle production reactor, the conditioning fluid from the supply chamber through the conditioning fluid inlet;

combining the plasma stream, the powder particles and the conditioning fluid, by the particle production chamber, thereby altering the powder particles and forming a mixture stream, wherein the altered powder particles are entrained within the mixture stream; and flowing the mixture stream to the mixture outlet of the particle production reactor.

18. The method of claim 17, wherein the conditioning fluid supply module comprises a conditioning fluid reservoir and an evaporator, and the method further comprises the steps of:

storing the conditioning fluid as a liquid gas, by the conditioning fluid reservoir;

receiving the conditioning fluid as a liquid gas from the conditioning fluid reservoir, by the evaporator;

evaporating the conditioning fluid to produce the conditioning fluid as a gas, by the evaporator; and receiving the conditioning fluid as a gas from the evaporator at the original pressure, by the pressure regulation module.

19. The method of claim 17, wherein the pressure regulation module comprises a pressure regulator and a pressure relief module fluidly coupled between the pressure regulator and the supply chamber, and the method further comprises the steps of:

receiving the conditioning fluid from the pressure regulator, by the pressure relief module; and reducing the pressure of the conditioning fluid prior to entry into the supply chamber by the pressure relief module venting a portion of the conditioning fluid to the environment.

20. The method of claim 17, wherein the pressure regulation module comprises a first pressure regulator, a second pressure regulator, and a third pressure regulator, and the method further comprises the steps of:

receiving the conditioning fluid from the conditioning fluid supply module at the original pressure, by the first pressure regulator;

reducing the pressure of the conditioning fluid from the original pressure to a second pressure, by the first pressure regulator;

receiving the conditioning fluid from the first pressure regulator at the second pressure, by the second pressure regulator;

reducing the pressure of the conditioning fluid from the second pressure to a third pressure, by the second pressure regulator;

receiving the conditioning fluid from the second pressure regulator at the third pressure, by the third pressure regulator; and reducing the pressure of the conditioning fluid from the third pressure to a fourth pressure, the third pressure regulator.

21. The method of claim 20, further comprising the step: supplying the overpressure gas to the particle production reactor when the pressure within the particle production reactor falls below the selected pressure.

22. The method of claim 9, further comprising the steps: configuring the first pressure regulator to receive the conditioning fluid at a pressure of 300 psi and to output the conditioning fluid at a pressure of 50 psi;
    configuring the second pressure regulator to receive the conditioning fluid at a pressure of 50 psi and to output the conditioning fluid at a pressure of 2 psi; and
configuring the third pressure regulator to receive the conditioning fluid at a pressure of 2 psi and to output the conditioning fluid at a pressure of 498 Pascals (2 inches of water).

* * * * *